(12) United States Patent
Nakamura et al.

(10) Patent No.: US 8,575,370 B2
(45) Date of Patent: Nov. 5, 2013

(54) METHOD FOR MANUFACTURING NEURAMINIC ACID DERIVATIVES

(71) Applicant: Daiichi Sankyo Co., Ltd., Tokyo (JP)

(72) Inventors: Yoshitaka Nakamura, Kanagawa (JP); Masakazu Wakayama, Kanagawa (JP); Kazuhiro Umeo, Kanagawa (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/795,050

(22) Filed: Mar. 12, 2013

(65) Prior Publication Data
US 2013/0197072 A1 Aug. 1, 2013

Related U.S. Application Data

(62) Division of application No. 12/450,699, filed as application No. PCT/JP2008/057557 on Apr. 11, 2008, now Pat. No. 8,455,659.

(30) Foreign Application Priority Data

Apr. 11, 2007 (JP) ................. 2007-103585

(51) Int. Cl.
*C07D 407/06* (2006.01)
(52) U.S. Cl.
USPC ........................................ 549/414
(58) Field of Classification Search
None
See application file for complete search history.

(56) References Cited

U.S. PATENT DOCUMENTS

| 5,495,027 | A | 2/1996 | Chandler et al. |
| 5,919,819 | A | 7/1999 | Andrews |
| 5,948,816 | A | 9/1999 | Ohira |
| 6,340,702 | B1 | 1/2002 | Honda et al. |
| 6,844,363 | B2 | 1/2005 | Murakami et al. |

FOREIGN PATENT DOCUMENTS

| EP | 0 882721 A | 12/1998 |
| JP | 2003-201235 A | 7/2003 |
| WO | WO 97/06157 A | 2/1997 |

OTHER PUBLICATIONS

Yamashita Makoto et al., CS-8958 (Ianinamivir octanoate hydrate), *Clinical microbiology*, 2010, p. 561-568, extra No. 37, Japan.
Andrews et al., "Synthesis and influenza virus sialidase inhibitory activity of analogues of 4-guanidino-Neu5Ac2en (Zanamirvir) modified in the glycerol side-chain", European Journal of Medical Chemistry, Editions Scientifique Elsevier, Paris, FR, vol. 34, 1 Jan. 1999, pp. 563-574, XP00216076.
Honda et al., "Synthesis and anti-influenza virus activity of 7-0-alkylated derivatives related to zanamivir", Bioorganic & Medicinal Chemistry Letters, vol. 12, No. 15, 2002, pp. 1925-1928, XP002511502, p. 1926, examples 3a-3c.
Honda et al., Bioorganic & Medicinal Chemistry Letters, vol. 12, No. 15, 2002, pp. 1921-1924.
Masuda et al., "Synthesis and anti-influenza evaluation of polyvalent sialidase inhibitors bearing 4-guanidino-Neu5Ac2en derivatives", Chem, Pharm. Bull., vol. 51, No. 12, 2003, pp. 1386-1398, XP001538673; p. 1388, examples 13a-13c.
Alaux et al., "Chemoenzymatic synthesis of a series of 4-substituted glutamate analogues and pharmacological characterization of human glutumate transporters subtypes 1-3", J. Med. Chem., vol. 48, 2005, pp. 7980-7992, XP002511504, p. 7982, fig. 3.
Norio Sugaya et al., Long-Acting Neuraminidase inhibitor Laninamivir Octanoate (CS-8958) versus Oseltamivir as Treatment for Children with Influenza Virus Infection, Antimicrobial Agents and Chemotherapy, Jun. 2010, p. 2575-2582, vol. 54 No. 6, American Society for Microbiology, Japan.

(Continued)

*Primary Examiner* — Kamal Saeed
(74) *Attorney, Agent, or Firm* — Holtz Holtz Goodman & Chick, P.C.

(57) ABSTRACT

Methods for manufacturing neuraminic acid compounds and synthetic intermediates of neuraminic acid compounds, including a method for manufacturing a compound represented by

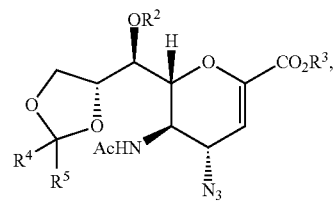

wherein $R^2$ represents a $C_1$-$C_4$ alkyl, $R^3$ represents a $C_1$-$C_6$ alkyl, $R^4$ and $R^5$ represent a hydrogen atom, a $C_1$-$C_6$ alkyl or a phenyl, or $R^4$ and $R^5$ together form a tetramethylene, a pentamethylene or an oxo, and Ac represents an acetyl, comprising reacting a compound represented by

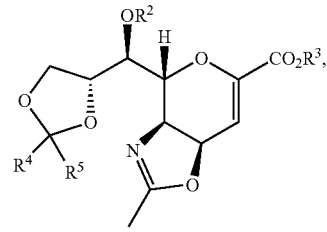

wherein $R^2$ represents a $C_1$-$C_4$ alkyl, $R^3$ represents a $C_1$-$C_6$ alkyl, $R^4$ and $R^5$ represent a hydrogen atom, a $C_1$-$C_6$ alkyl or a phenyl, or $R^4$ and $R^5$ together form a tetramethylene, a pentamethylene or an oxo, with trimethylsilyl azide in the presence of a Lewis acid.

2 Claims, No Drawings

(56) References Cited

OTHER PUBLICATIONS

Akira Watanabe et al., Long-Acting Neuraminidase Inhibitor Laninamivir Octanoate versus Oseltamivlr for Treatment of influenza: A Double-Blind, Randomized, Noninferiority Clinical Trial, Clinical Infectious Disease, Nov. 15, 2010, p. 1167-1175, vol. 51 No. 10, Infectious Disease, Nov. 15, 2010, p. 1167-1175, vol. 51 No. 10, Infectious Disease Society of America, Japan.

Ha T. Nguyen et al., Assessment of Pandemic and Seasonal Influenza A (HiNi) Virus Susceptibility to Neuraminidase Inhibitors in Three Enzyme Activity Inhibition Assays, Antimicrobial Agents and Chemotherapy, Sep. 2010, p. 3671-3677, vol. 54 No. 9, American Society for Microbiology, Japan.

Akira Watanabe et al, 2. CS-8958, Virus Report, 2009, p. 122-129, vol. 6 No. 2, Japan.

Takeshi Honda et al., Synthesis and Anti-Influenza Virus Activity of 4-Guanidino-7-substituted Neu5Ac2en Derivatives, Bioorganic & Medicinal Chemistry Letters, 2002, p. 1921-1924, vol. 12, Elsevier Science Ltd., Japan.

Takeshi Honda at al., Synthesis and Anti-Influenza Virus Activity of 7-O-Alkylated Derivatives Related to Zanamivir, Bloorganic & Medicinal Chemistry Letters, 2002, p. 1925-1928, vol, 12, Elsevier Science Ltd., Japan.

Takeshi Honda et al., Synthesis and in vivo influenza virus-inhibitory effect of ester prodrug of 4-guanidino-7-O-methly-Neu5Ac2en, Bioorganic & Medicinal Chemistry Letters, 2009, p. 2938-2940, vol. 19, Elsevier Ltd., Japan.

Takeshi Honda at al., Synthesis of 4-Guanidlno-7-Modifled-Neu5Ac2en Derivatives and Their Biological Activities as Influenza Sialidase Inhibitors, J. Syn Org Chem, 2009, p. 1105-1104, vol. 67 No. 11, Japan.

Kumiko Koyama et al., CS-8958, a Prodrug of the Novel Neuraminidase Inhibitor R-125459, Demonstrates a Favorable Long-Retention Profile in the Mouse Respiratory Tract, Antimicrobial Agents and Chemotherapy, Nov. 2009, p. 4845-4851, vol. 53 No. 11, American Society for Microbiology, Japan.

K. Koyama et al., Pharmacokinetics and disposition of CS-8958, a long-acting prodrug of the novel neuraminidase inhibitor laninamivir in rats, Xenobiotica, 2010, p. 207-216, vol. 40 No. 3, Informa UK Ltd, Japan.

Yoshiyuki Kobayashi PHD, at al., LANI (Long-Acting Neuraminiclase Inhibitor) -CS-8958, from bench to bed, Medical Science Digest, 2006, p. 631-635, vol. 34 No, 14, Daiichi Sankyo Co. Ltd. Japan.

Chemistry, 2009, p. 18-22, vol. 64 No. 10, Japan.

Yoshiyuki Kobayashi PHD. at al., LANI (Long-Acting Neuraminidase Inhibitor) , Medical Science Digest, 2009, p. 461-466, vol. 35 No. 11, Daiichi Sankyo Co. Ltd., Japan.

Yoshiyuki Kobayashi PHD. et al., LANI (Long-Acting Neuraminidase Inhibitor)-CS-8955, a single inhaled drug for the treatment of Influenza, The Cell Dec. 2009, p. 42-45, vol. 41 No. 14, Daiichi Sankyo Co. Ltd., Japan.

Makoto Yamashita et al., CS-8958, a Prodrug of the New Neuraminidase Inhibitor R-125489, Shows Long-Acting Anting Anti-Influenza Virus Activity, Antimicrobial Agents and Chemotherapy, Jan. 2009, p. 186-192, vol. 53 No. 1, American Society for Microbiology, Japan.

Yasushi Itoh et al., In vitro and in vivo characterization of new swine-origin H1N1 influenza viruses, Nature, Aug. 20, 2009, p. 1021-1025, vol. 460 No. 20, Macmillan Publishers Limited, Japan.

Maki Kiso et al., Efficacy of the New Neuraminidase Inhibitor CS-8958 against H5N1 Influenza Viruses, PLoS Pathogens, Feb. 2010, p. e1000786, vol. 6 No. 2, Japan.

Shuku Kubo et al., Laninamivir Prodrug CS-8958, a Long-Acting Neuraminidase Inhibitor, Shows Superior Anti-Influenza Virus Activity after a Single Administration, Antimicrobial Agents and Chemotherapy, Mar. 2010, p. 1256-1264, vol, 54 No. 3, American Society of Microbiology, Japan.

Maki Kiso et al., Characterization of Oseltamivir-Resistant 2009 H1N1 Pandemic Influenza A Viruses, PLoS Pathogens, Aug. 2010, p. e1001079, vol. 6 No. 8, Japan.

Shuku Kubo et al., In vitro and in vivo effects of a long-acting anti-influenza agent CS-8958 (laninamivir octonoate, Inavar® against pandemic (H1N1) 2009 influenza viruses, Japanese Journal of Antibiotics, Oct. 2010, p. 337-346, vol. 63, No. 5, Japan.

Makoto Yamashita et al., Influenza, 2004, p. 307-31, vol, 5 No. 4, Japan.

Makoto Yamashita, New anti-influenza compound, second generation anti-influenza compound CS-8958, Antibiotics & Chemotherapy, 2005, p. 65-71, vol. 21 No. 12, Japan.

Makoto Yamashita et al., Allergology & immunology, 2006, p. 59-67, vol. 13 No. 11, Japan.

Influenza, 2009, p. 72-76, vol. 10 No. 3, Japan.

Makoto Yamashita et al., New Anti-influenza Compounds, Anti Aging Medicine, 2009, p. 841-849, vol. 5 No. 6, Japan.

Makoto Yamashita et al., Function of neuraminidase of influenza virus and anti influenza compounds by its inhibition, Short Review, 2009, p. 1284-1291, vol. 54 No. 10, Japan.

Medicine and Drug Journal, 2010, p. 767-771, vol, 46 No. 2, Japan.

Makoto Yamashita et al., CS-8958 (laninamivir octanoate hydrate), Clinical microbiology, 2010, p. 561-568. extra No. 37, Japan.

Hitoshi Ishizuka et al, Clinical Pharmacokinetics of Laninamivir, a Novel Long-Acting Neuraminidase Inhibitor, After single and Multiple Inhaled Doses of its Prodrug, CS-8958, in Healthy Male Volunteers, The Journal of Clinical Pharmacology, 2010, p. 1319-1329, vol. 50. The Author(s), Japan.

Hitoshi Ishizuka et al., Assessment of Effects of Renal Impairment on the Pharmacokinetic Profile of Laninamivir, A Novel Neuraminidase Inhibitor, After a Single Inhaled Dose of its Prodrug, CS-8958, The Journal of Clinical Pharmacology, Mar. 2, 2010, The American College of Clinical Pharmacology, Japan.

Stanoeva et al., "Synthesis of 1-substituted 2,9-trioxatricyclo[4.3.1. 0<3,8>decanes", Tetrahedron, Elsevier Science Publishers, Amsterdam, NL, vol. 60, No. 23, May 31, 2004, pp. 5077-5084, XP004509484.

Peter P. T. Sah, "Esters of ortho-acetic acid", Journal of the American Chemical Society, vol. 50, 1928, pp. 516-518, XP002511505.

Reitter et al, "Uber die Darstellung einiger aliphatischer Orthoketonather und Orthosaureester", Chemische Berichte, vol. 40, 1907, pp. 3020-3025, XP002511506, p. 3021.

European Office Action in 11003967.4 dated Jul. 12, 2011.
European Office Action in 11003968.2 dated Jul. 12, 2011.
European Office Action in 11003969.0 dated Jul. 15, 2011.
International Search Report for PCT/JP2008/057557 mailed on Feb. 10, 2009.
Written Opinion for Fct/JP2008/057557 mailed Feb. 10, 2009.
Makoto Yamashita, Laninamivir and its prodrug. CS-8958; long-acting neuraminidase inhibitors for the treatment of influenza, Antiviral Chemistry & Chemotherapy, 2010, p. 71-84, vol. 21, Biological Research Laboratories, Daiichi Sankyo Col, Ltd. Tokyo, Japan.

METHOD FOR MANUFACTURING NEURAMINIC ACID DERIVATIVES

CROSS-REFERENCE TO RELATED APPLICATIONS

This application is a divisional application of application Ser. No. 12/450,699 filed Oct. 7, 2009, which is the United States national phase application under 35 USC 371 of International application PCT/JP2008/057557 filed Apr. 11, 2008. The entire contents of each of application Ser. No. 12/450,699 and International application PCT/JP2008/057557 are hereby incorporated by reference herein.

TECHNICAL FIELD

The present invention relates to a method for manufacturing neuraminic acid derivatives which have neuraminidase inhibitory activity, and to synthetic intermediates of the neuraminic acid derivatives and methods for their manufacture. In addition, the present invention relates to neuraminic acid derivatives having high purity.

BACKGROUND ART

A compound represented by the formula (I):

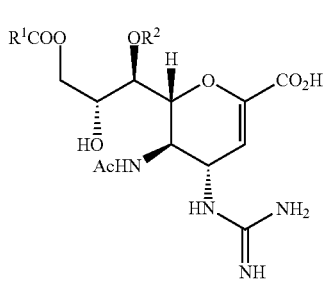

(I)

[wherein $R^1$ represents a $C_1$-$C_{19}$ alkyl group and $R^2$ represents a $C_1$-$C_4$ alkyl group] or a pharmacologically, acceptable salt thereof is known to have excellent neuraminidase inhibitory activity and therefore to be useful as a drug for treatment or prevention of influenza (Patent Document 1 or 2).

A trifluoroacetic acid salt of a compound represented by the formula (III):

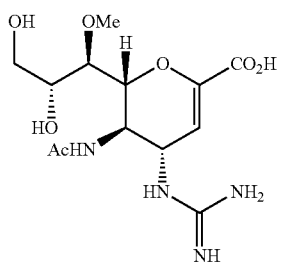

(III)

is known to have excellent neuraminidase inhibitory activity and therefore to be useful as a drug for treatment or prevention of influenza (Non-patent Document 1 or 2).

Process W is known as a method for manufacturing a compound represented by the formula (Ia), which is embraced in a compound represented by the formula (I) or a pharmacologically acceptable salt thereof, [hereinafter also referred to as "compound (Ia)"; the same shall be applied with respect to other formulas] (Patent Document 1). In Process W, n-Hep represents a 1-heptyl group.

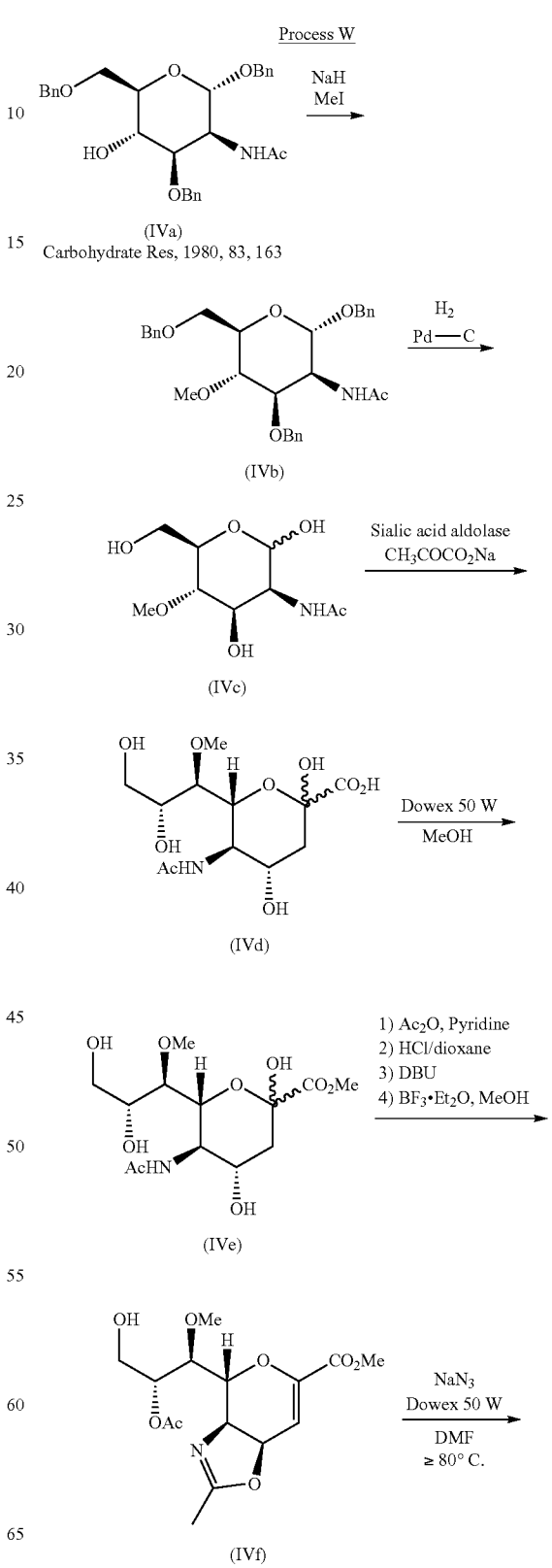

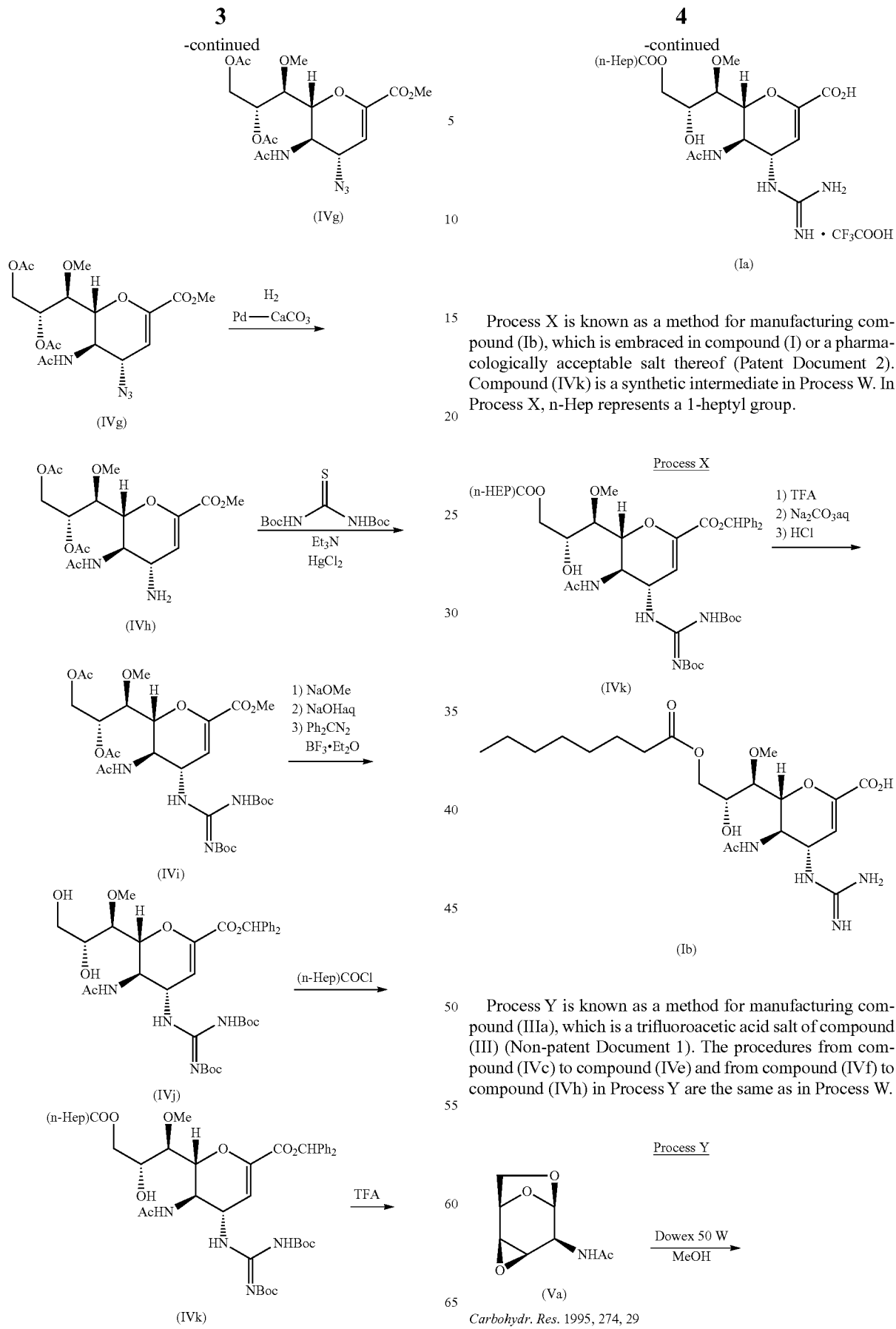

Process X is known as a method for manufacturing compound (Ib), which is embraced in compound (I) or a pharmacologically acceptable salt thereof (Patent Document 2). Compound (IVk) is a synthetic intermediate in Process W. In Process X, n-Hep represents a 1-heptyl group.

Process Y is known as a method for manufacturing compound (IIIa), which is a trifluoroacetic acid salt of compound (III) (Non-patent Document 1). The procedures from compound (IVc) to compound (IVe) and from compound (IVf) to compound (IVh) in Process Y are the same as in Process W.

*Carbohydr. Res.* 1995, 274, 29

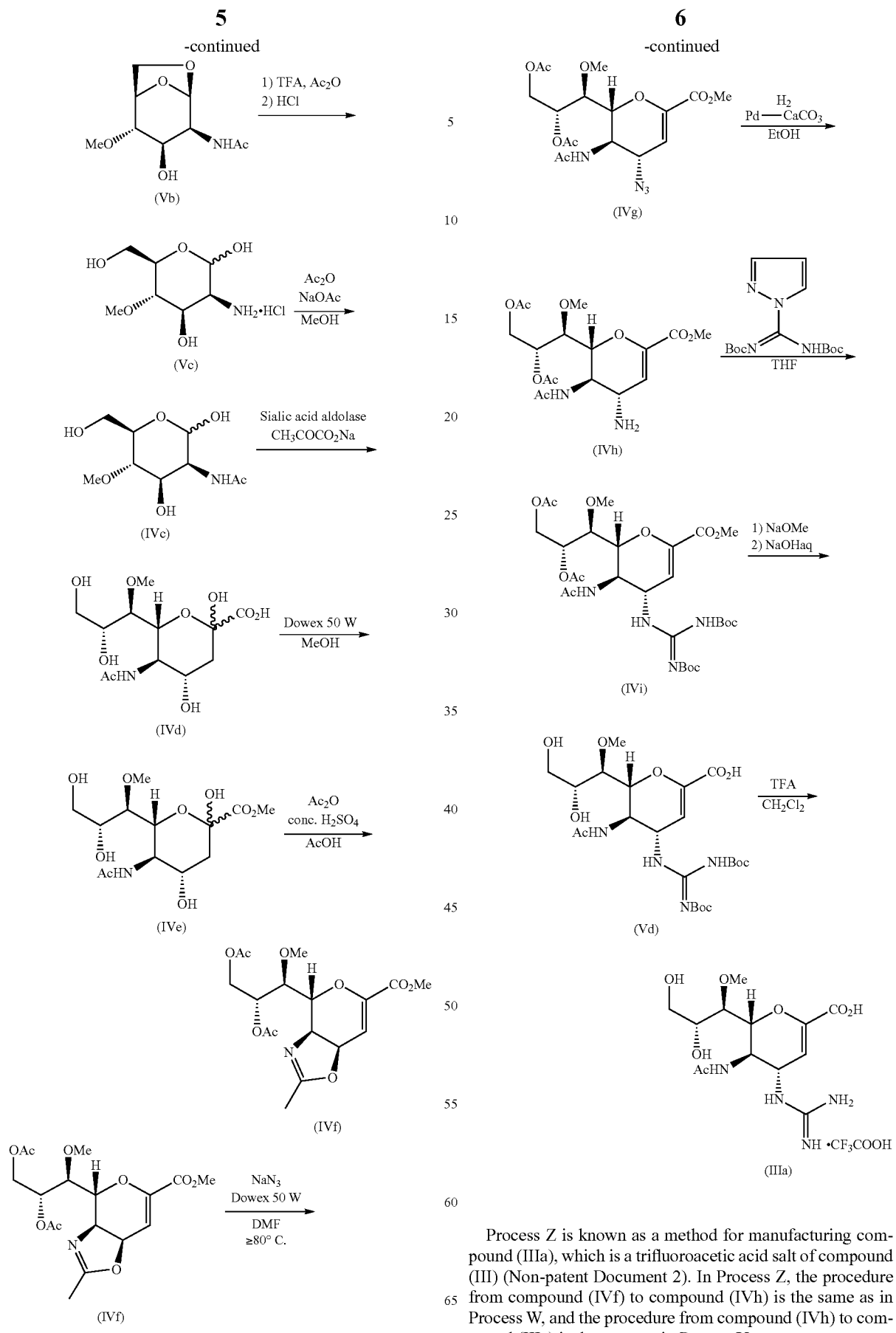
Process Z is known as a method for manufacturing compound (IIIa), which is a trifluoroacetic acid salt of compound (III) (Non-patent Document 2). In Process Z, the procedure from compound (IVf) to compound (IVh) is the same as in Process W, and the procedure from compound (IVh) to compound (IIIa) is the same as in Process Y.

Process Z

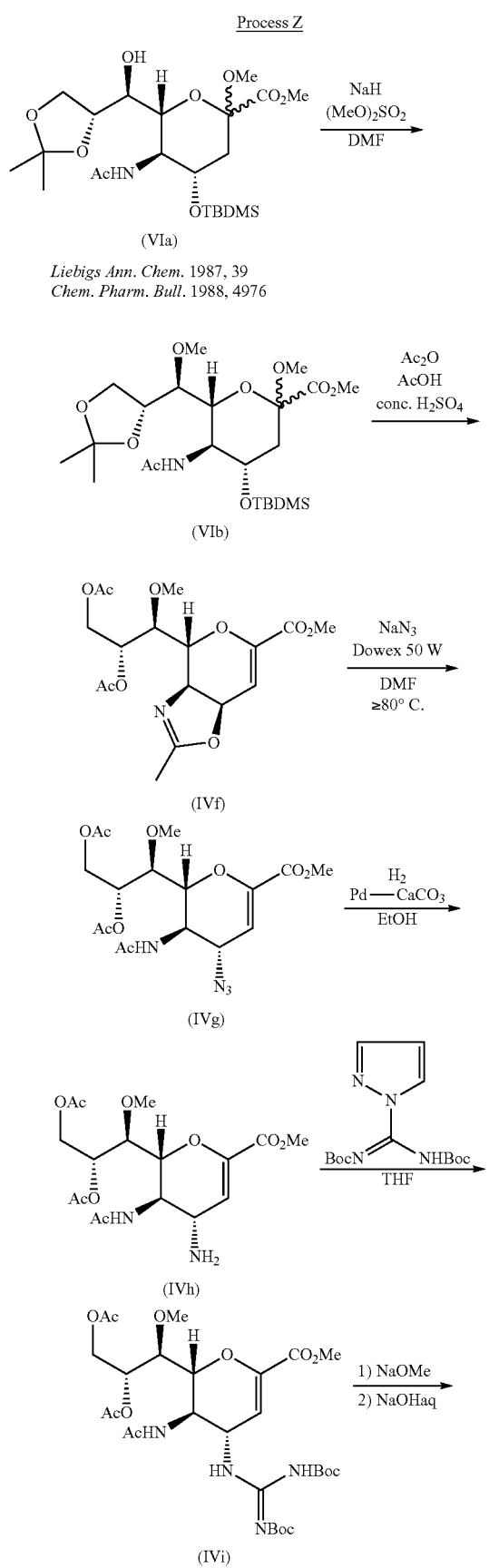

*Liebigs Ann. Chem.* 1987, 39
*Chem. Pharm. Bull.* 1988, 4976

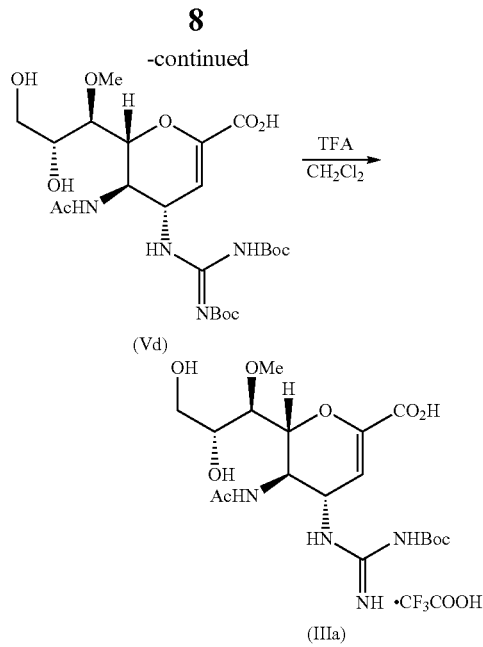

From the viewpoint of industrial production, the aforementioned Process W, Process Y, or Process Z could be improved in points such as the following:

[Process W]
(1) the overall yield is low since a procedure with a low yield is included [overall yield of compound (Ia): 0.2%];
(2) N-methylation of an acetamide group occurs as a side reaction of methylation reaction of a hydroxy group [production procedure of compound (IVb)];
(3) an inefficient enzyme reaction is included [production procedure of compound (IVd)];
(4) a hazardous azidation reaction at high temperature is included [production procedure of compound (IVg)]; or
(5) in the acylation reaction, (a) protection of a carboxyl group is necessary, (b) 2,3-diacylated product is generated as by-product, and (c) purification by silica gel column chromatography is necessary to remove octanoic acid derived from the reagent [production procedure of compound (IVk)];

[Process Y]
(1) the overall yield is low since a procedure with a low yield is included [yield of compound (Va): 34%, overall yield from compound (Va) to compound (IIIa): 10 to 23%, resulting in 3 to 8%];
(2) an inefficient enzyme reaction is included [production procedure of compound (IVd)]; or
(3) a hazardous azidation reaction at high temperature is included [production procedure of compound (IVg)];

[Process Z]
(1) the overall yield is low since a procedure with a low yield is included [yield of compound (VIa): 35%, overall yield from compound (VIa) to compound (IIIa): 1 to 33%, resulting in 0.4 to 12%];
(2) an expensive silyl protective group is used;
(3) N-methylation of an acetamide group occurs as a side reaction of the methylation reaction of a hydroxy group [production procedure of compound (IVb)]; or
(4) a hazardous azidation reaction at high temperature is included [production procedure of compound (IVg)].

[Patent Document 1] U.S. Pat. No. 6,340,702 (corresponding to Japanese Patent No. 3209946)

[Patent Document 2] U.S. Pat. No. 6,844,363 (corresponding to Japanese Patent Application No. 2002-012590)

[Non-patent Document 1] T. Honda et al., Bioorganic Medicinal Chemistry Letters, 2002, pp. 1921-1924

[Non-patent Document 2] T. Honda et al., Bioorganic Medicinal Chemistry Letters, 2002, pp. 1925-1928

As a result of conducting extensive studies on methods for manufacturing neuraminic acid derivatives, the inventors of the present invention have found a novel method for manufacturing neuraminic acid derivatives via novel synthetic intermediates of the present invention that is superior to publicly known manufacturing methods from an industrial perspective, and have found that neuraminic acid derivatives with high purity can be obtained in high yield by the manufacturing method. The present invention has been completed based on the aforementioned findings.

SUMMARY OF THE INVENTION

The present invention provides a method for manufacturing neuraminic acid derivatives which have neuraminidase inhibitory activity, and synthetic intermediates of the neuraminic acid derivatives and methods for their manufacture. In addition, the present invention provides neuraminic acid derivatives having high purity.

The present invention provides a method for manufacturing a neuraminic acid derivative shown by the following Process A:

Process A

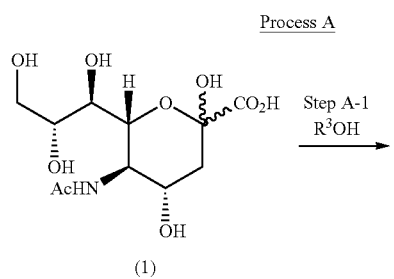

(1)

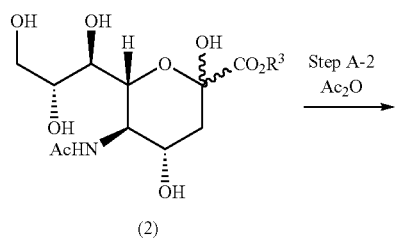

(2)

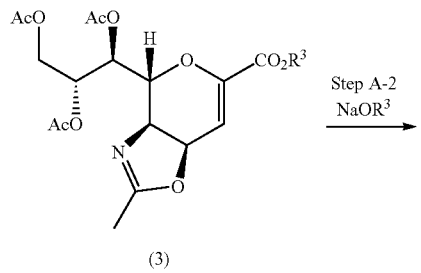

(3)

-continued

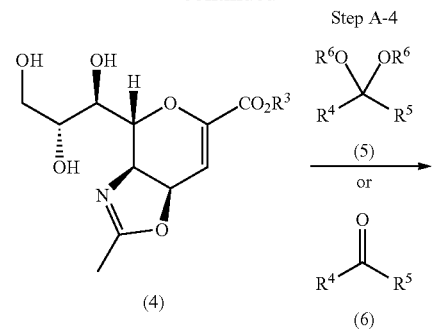

(4)          (6)

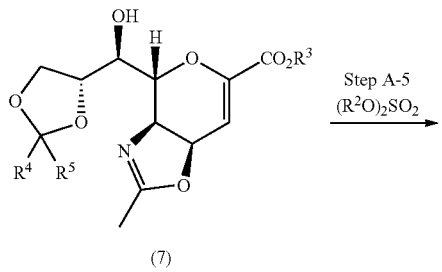

(7)

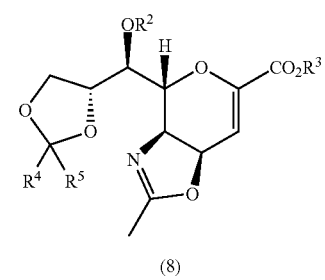

(8)

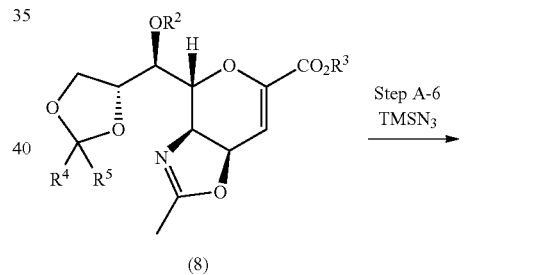

(8)

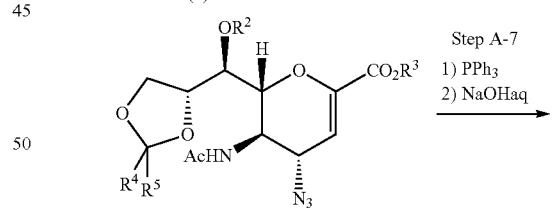

(9)

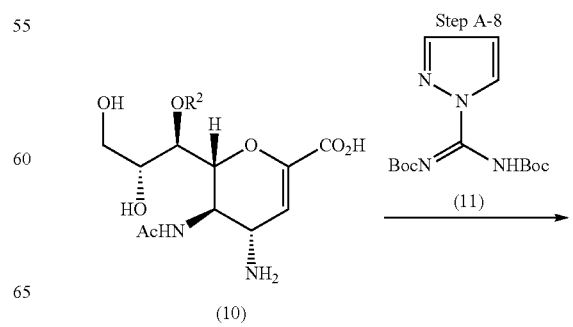

(10)          (11)

-continued

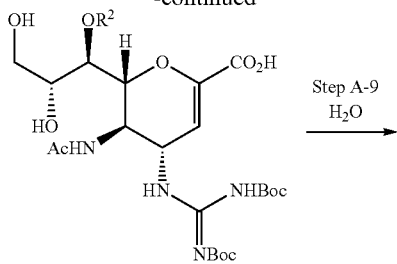

(12)

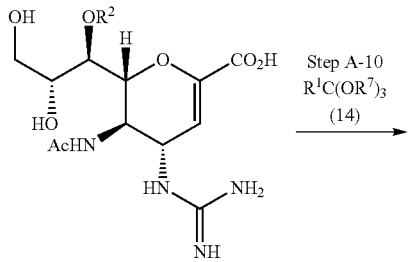

(13)

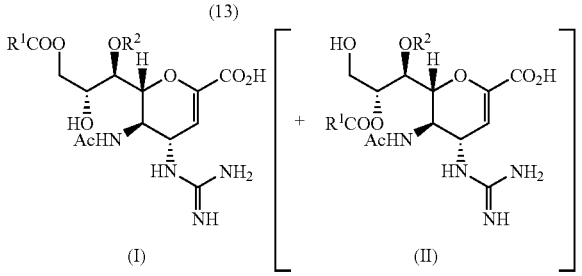

In the aforementioned Process A, $R^1$ represents a $C_1$-$C_{19}$ alkyl group, $R^2$ represents a $C_1$-$C_4$ alkyl group, $R^3$, $R^6$ and $R^7$, independently from one another, represent a $C_1$-$C_6$ alkyl group, $R^4$ and $R^5$, independently from each other, represent a hydrogen atom, a $C_1$-$C_6$ alkyl group or a phenyl group, or $R^4$ and $R^5$ together form a tetramethylene group, a pentamethylene group or oxo group except that $R^4$ and $R^5$ in compound (6) do not form an oxo group. Here, Ac represents an acetyl group, Boc represents a tert-butoxycarbonyl group, and Ph represents a phenyl group. The same applies for these three groups hereinafter.

According to one aspect of the present invention, there is provided

[1] a method for manufacturing a compound represented by the formula (7):

(7)

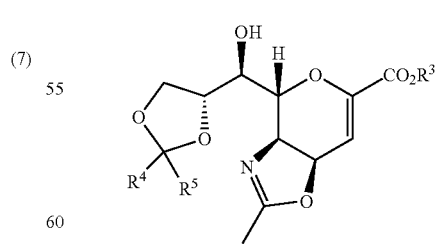

[wherein $R^3$ represents a $C_1$-$C_6$ alkyl group, and $R^4$ and $R^5$, independently from each other, represent a hydrogen atom, a $C_1$-$C_6$ alkyl group or a phenyl group, or $R^4$ and $R^5$ together form a tetramethylene group, a pentamethylene group or an oxo group], comprising:

allowing a compound represented by the formula (4):

(4)

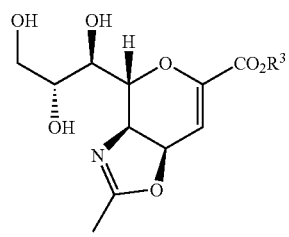

[wherein $R^3$ represents a $C_1$-$C_6$ alkyl group] to react with a compound represented by the formula (5):

(5)

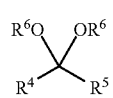

[wherein $R^4$ and $R^5$, independently from each other, represent a hydrogen atom, a $C_1$-$C_6$ alkyl group or a phenyl group, or $R^4$ and $R^5$ together form a tetramethylene group, a pentamethylene group or an oxo group, and $R^6$ represents a $C_1$-$C_6$ alkyl group], or with a compound represented by the formula (6):

(6)

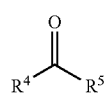

[wherein $R^4$ and $R^5$, independently from each other, represent a hydrogen atom, a $C_1$-$C_6$ alkyl group or a phenyl group, or $R^4$ and $R^5$ together form a tetramethylene group or a pentamethylene group] except that $R^4$ and $R^5$ in compound (7) do not together form an oxo group when compound (6) is used,

[2] the manufacturing method as described in [1], wherein a compound represented by the formula (7) is manufactured by the reaction of a compound represented by the formula (4) with a compound represented by the formula (5), and $R^3$ is a methyl group, $R^4$ and $R^5$ together form an oxo group, and the compound represented by the formula (5) is dimethyl carbonate,

[3] a compound represented by the formula (7):

(7)

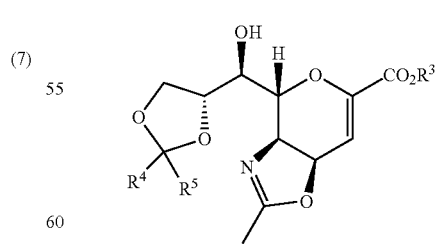

[wherein $R^3$ represents a $C_1$-$C_6$ alkyl group, $R^4$ and $R^5$, independently from each other, represent a hydrogen atom, a $C_1$-$C_6$ alkyl group or a phenyl group, or $R^4$ and $R^5$ together form a tetramethylene group, a pentamethylene group or an oxo group],

[4] the compound as described in [3], wherein $R^3$ is a methyl group, and $R^4$ and $R^5$ together form an oxo group,

[5] a method for manufacturing a compound represented by the formula (9):

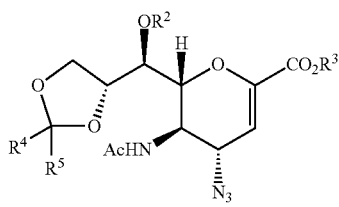

(9)

[wherein $R^2$ represents a $C_1$-$C_4$ alkyl group, $R^3$ represents a $C_1$-$C_6$ alkyl group, and $R^4$ and $R^5$, independently from each other, represent a hydrogen atom, a $C_1$-$C_6$ alkyl group or a phenyl group, or $R^4$ and $R^5$ together form a tetramethylene group, a pentamethylene group or an oxo group], comprising:

allowing a compound represented by the formula (8):

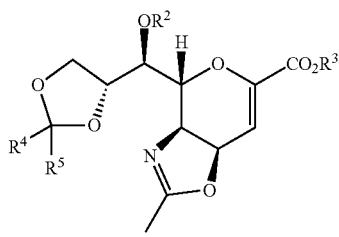

(8)

[wherein $R^2$ represents a $C_1$-$C_4$ alkyl group, $R^3$ represents a $C_1$-$C_6$ alkyl group, $R^4$ and $R^5$, independently from each other, represent a hydrogen atom, a $C_1$-$C_6$ alkyl group or a phenyl group, or $R^4$ and $R^5$ together form a tetramethylene group, a pentamethylene group or an oxo group] to react with trimethylsilyl azide in the presence of a Lewis acid,

[6] the manufacturing method as described in [5], wherein $R^2$ is a methyl group, $R^3$ is a methyl group, $R^4$ and $R^5$ together form an oxo group, and the Lewis acid is titanium (IV) isopropoxide,

[7] a method for manufacturing a compound represented by the formula (13):

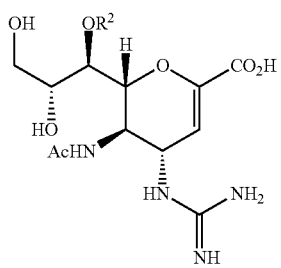

(13)

[wherein $R^2$ represents a $C_1$-$C_4$ alkyl group], comprising:
allowing a compound represented by the formula (12):

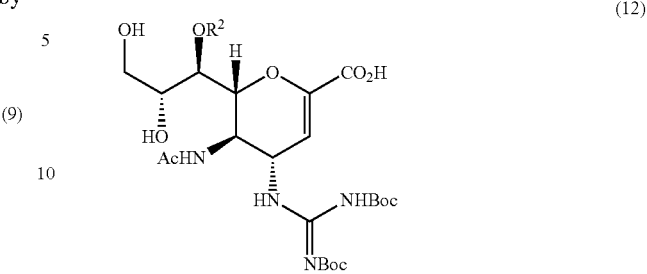

(12)

[wherein $R^2$ represents a $C_1$-$C_4$ alkyl group] to react with water,

[8] the manufacturing method as described in [7], wherein $R^2$ is a methyl group,

[9] a compound represented by the formula (13):

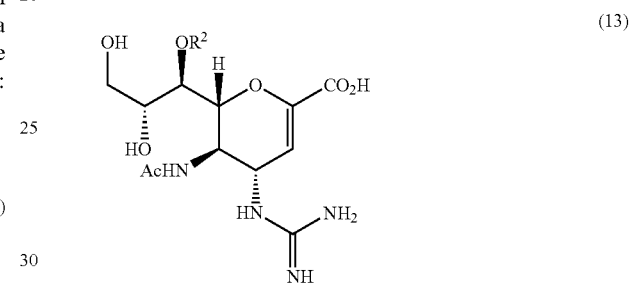

(13)

[wherein $R^2$ represents a $C_1$-$C_4$ alkyl group],

[10] the compound as described in [9], wherein $R^2$ is a methyl group,

[11] a method for manufacturing a compound represented by the formula (I):

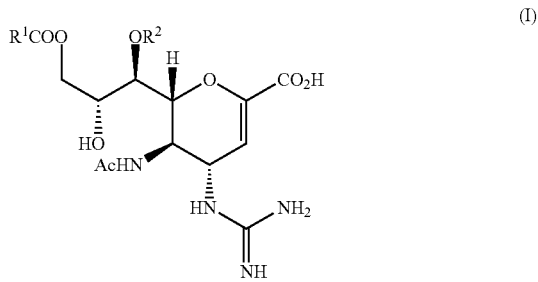

(I)

[wherein $R^2$ represents a $C_1$-$C_{19}$ alkyl group and $R^2$ represents a $C_1$-$C_4$ alkyl group], [here, the compound represented by the formula (I) may include a compound represented by the formula (II):

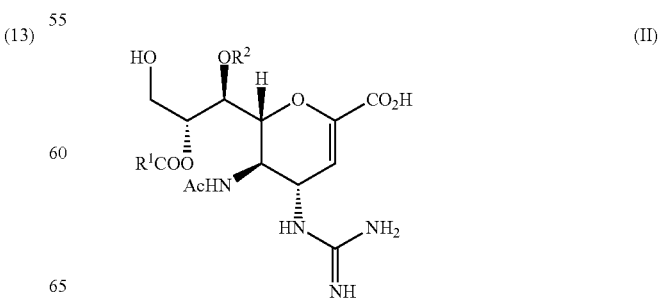

(II)

[wherein $R^1$ and $R^2$ have the same meanings as in the formula (I)], or a pharmacologically acceptable salt thereof comprising:

allowing a compound represented by the formula (13):

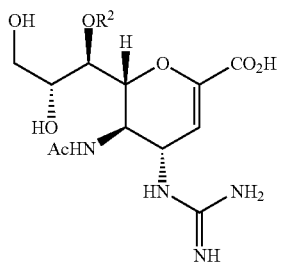

(13)

[wherein $R^2$ represents a $C_1$-$C_4$ alkyl group] to react with a compound represented by the formula $R^1C(OR^7)_3$ [wherein $R^1$ represents a $C_1$-$C_{19}$ alkyl group and R' represents a $C_1$-$C_6$ alkyl group], or a pharmacologically acceptable salt thereof,

[12] the manufacturing method as described in [11], wherein $R^1$ is a 1-heptyl group, $R^2$ is a methyl group, and $R^7$ is a methyl group,

[13] a method for manufacturing a compound represented by the formula (I):

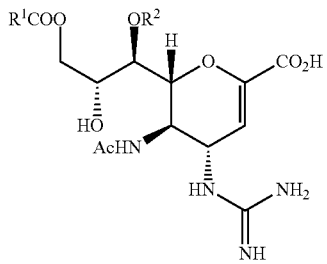

(I)

[wherein $R^1$ represents a $C_1$-$C_{19}$ alkyl group and $R^2$ represents a $C_1$-$C_4$ alkyl group], [here, the compound represented by the formula (I) may include a compound represented by the formula (II):

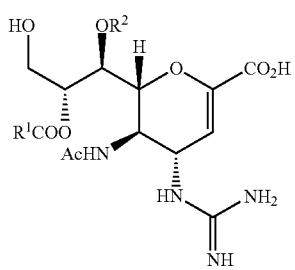

(II)

[wherein $R^1$ and $R^2$ have the same meanings as in the formula (I)] or pharmacologically acceptable salt thereof, comprising: allowing a compound represented by the formula (13):

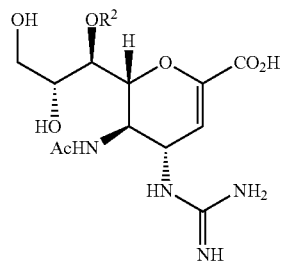

(13)

[wherein $R^2$ represents a $C_1$-$C_4$ alkyl group] to react with a compound represented by the formula (15):

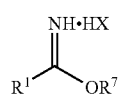

(15)

[wherein $R^1$ represents a $C_1$-$C_{19}$ alkyl group, $R^7$ represents a $C_1$-$C_6$ alkyl group, and X represents Cl, Br, I, $HSO_4$ or $NO_3$], and with a compound represented by the formula $R^7$—OH [wherein $R^7$ represents a $C_1$-$C_6$ alkyl group],

[14] the manufacturing method as described in [13], wherein $R^1$ is a 1-heptyl group, $R^2$ is a methyl group, $R^7$ is a methyl group, and X is Cl,

[15] a method for manufacturing a compound represented by the formula (Ib):

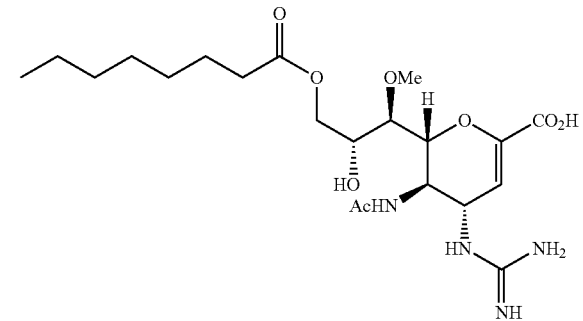

(Ib)

[wherein Me represents a methyl group (the same applies hereinafter), and the compound represented by the formula (Ib) may include a compound represented by the formula (IIb):

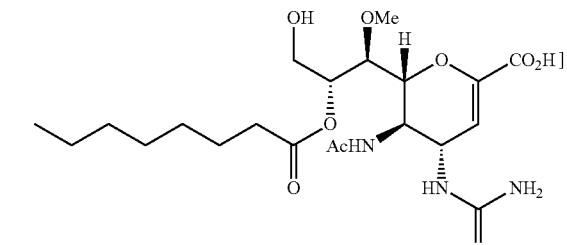

(IIb)

or a pharmacologically acceptable salt thereof, which includes at least one manufacturing method described in any one of [2], [6] and [8] as part of the production procedure,

[16] a method for manufacturing a compound represented by the formula (Ib):

(Ib)

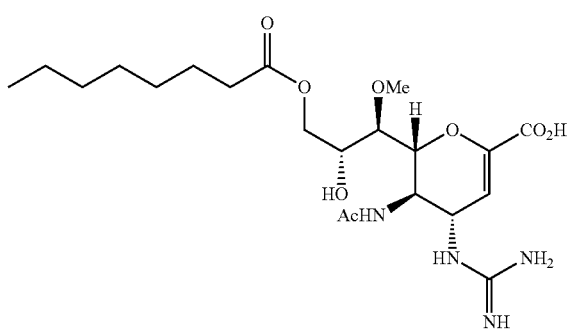

[wherein the compound represented by the formula (Ib) may include a compound represented by the formula (IIb):

(IIb)

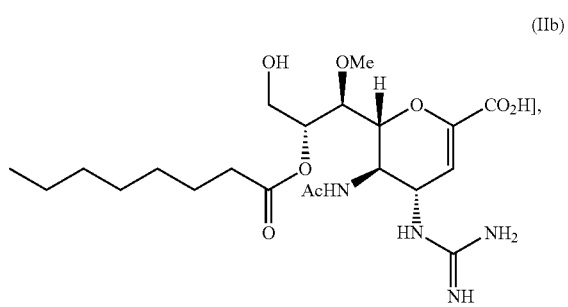

or a pharmacologically acceptable salt thereof, which proceeds via at least one compound described in either one of [4] and [10],

[17] a compound represented by the formula (I):

(I)

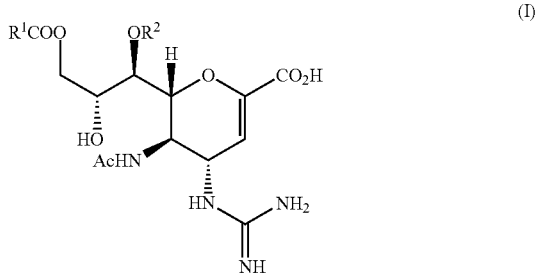

[wherein $R^1$ represents a $C_1$-$C_{19}$ alkyl group and $R^2$ represents a $C_1$-$C_4$ alkyl group], [here, the compound represented by the formula (I) may include a compound represented by the formula (II):

(II)

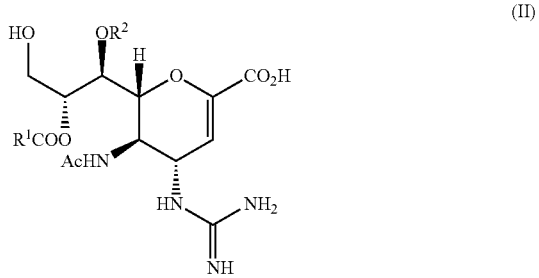

[wherein $R^1$ and $R^2$ have the same meanings as in the formula (I)]] having a chemical purity of 97 wt % or higher, [wherein in the case where the compound represented by the formula (II) is included, the chemical purity of the mixture of the compound represented by the formula (I) and the compound represented by the formula (II) is 97 wt % or higher], or a pharmacologically acceptable salt thereof,

[18] the compound represented by the formula (I), which may include the compound represented by the formula (II), or pharmacologically acceptable salt thereof as described in [17], wherein the chemical purity is 99 wt % or higher,

[19] the compound represented by the formula (I), which may include the compound represented by the formula (II), or pharmacologically acceptable salt thereof as described in [17], wherein the chemical purity is 99.5 wt % or higher,

[20] the compound represented by the formula (I), which may include the compound represented by the formula (II), as described in any one of [17] through [19], wherein $R^1$ is a 1-heptyl group and $R^2$ is a methyl group,

[21] a compound represented by the formula (I):

(I)

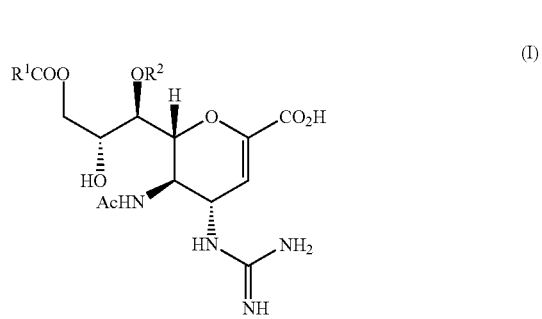

[wherein $R^1$ represents a $C_1$-$C_{19}$ alkyl group and $R^2$ represents a $C_1$-$C_4$ alkyl group], [here, the compound represented by the formula (I) may include a compound represented by the formula (II):

(II)

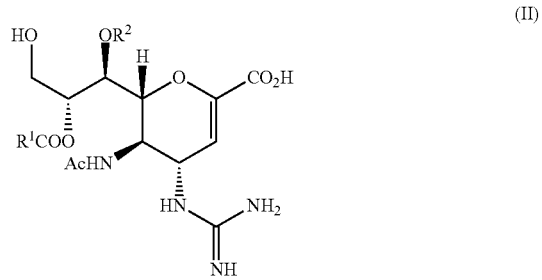

[wherein $R^1$ and $R^2$ have the same meanings as in the formula (I)]], or a pharmacologically acceptable salt thereof, containing a compound represented by the formula (VII):

(VII)

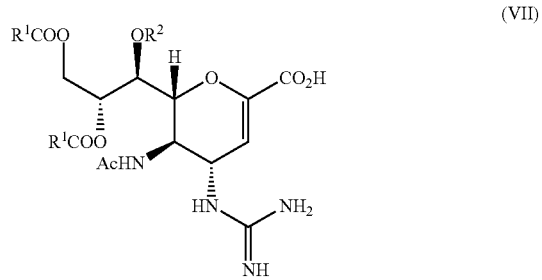

[wherein R¹ and R² represent have the same meanings as in the formula (I)] in an amount of 0.5 wt % or less,

[22] a compound represented by the formula (I), which may include the compound represented by the formula (II), or pharmacologically acceptable salt thereof as described in [21], containing the compound represented by the formula (VII) in an amount of 0.3 wt % or less,

[23] a compound represented by the formula (I), which may include the compound represented by the formula (II), or pharmacologically acceptable salt thereof as described in [21], containing the compound represented by the formula (VII) in an amount of 0.1% or less,

[24] a compound represented by the formula (I), which may include the compound represented by the formula (II), as described in any one of [21] through [23], wherein R¹ is a 1-heptyl group and R² is a methyl group,

[25] a compound represented by the formula (I):

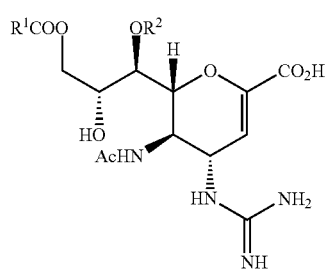

[wherein R¹ represents a $C_1$-$C_{19}$ alkyl group and R² represents a $C_1$-$C_4$ alkyl group], [here, the compound represented by the formula (I) may include a compound represented by the formula (II):

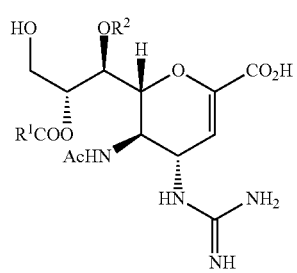

[wherein R¹ and R² have the same meanings as in the formula (I)]], or a pharmacologically acceptable salt thereof, containing a compound represented by the formula (VIII):

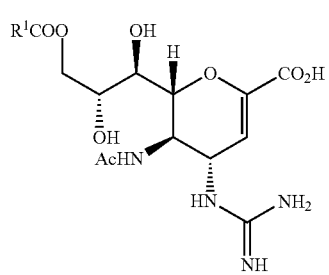

[wherein R¹ has the same meaning as the formula (I)] in an amount of 0.5 wt % or less,

[26] a compound represented by the formula (I), which may include the compound represented by the formula (II), or pharmacologically acceptable salt thereof as described in [25], containing the compound represented by the formula (VIII) in an amount of 0.3 wt % or less,

[27] a compound represented by the formula (I), which may include the compound represented by the formula (II), or pharmacologically acceptable salt thereof as described in [25], containing the compound represented by the formula (VIII) in an amount of 0.1 wt % or less,

[28] a compound represented by the formula (I), which may include the compound represented by the formula (II) as described in any one of [25] through [27], wherein R¹ is a 1-heptyl group and R² is a methyl group,

[29] a compound represented by the formula (I):

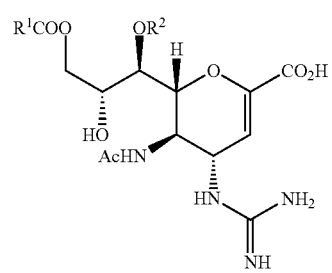

[wherein R¹ represents a $C_1$-$C_{19}$ alkyl group and R² represents a $C_1$-$C_4$ alkyl group], [here, the compound represented by the formula (I) may include a compound represented by the formula (II):

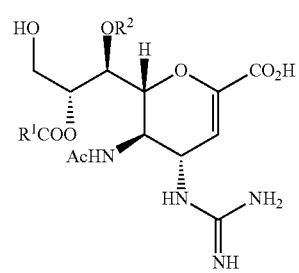

[wherein R¹ and R² have the same meanings as in the formula (I)]], or a pharmacologically acceptable salt thereof, containing a compound represented by the formula (13):

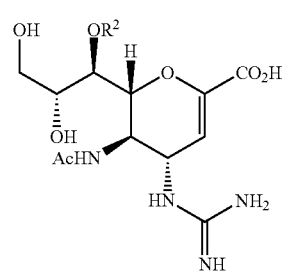

[wherein R² has the same meaning as in the formula (I)] in an amount of 0.5 wt % or less,

[30] a compound represented by the formula (I), which may include the compound represented by the formula (II), or pharmacologically acceptable salt thereof as described in [29], containing the compound represented by the formula (13) in an amount of 0.3 wt % or less,

[31] a compound represented by the formula (I), which may include the compound represented by the formula (II), or pharmacologically acceptable salt thereof as described in [29], containing the compound represented by the formula (13) in an amount of 0.1 wt % or less,

[32] a compound represented by the formula (I), which may include the compound represented by the formula (II) as described in any one of [29] through [31], wherein R¹ is a 1-heptyl group and R² is a methyl group,

[33] a compound represented by the formula (I), which may include a compound represented by the formula (II), as described in any one of [17] through [32], wherein the composition ratio of the compound represented by the formula (I) and the compound represented by the formula (II) is 90:10 to 100:0 by weight,

[34] a compound represented by the formula (I), which may include the compound represented by the formula (II), as described in any one of [17] through [32], wherein the composition ratio of the compound represented by the formula (I) and the compound represented by the formula (II) is 92:8 to 100:0 by weight,

[35] a compound represented by the formula (I), which may include the compound represented by the formula (II), as described in any one of [17] through [32], wherein the composition ratio of the compound represented by the formula (I) and the compound represented by the formula (II) is 95:5 to 100:0 by weight,

[36] a method for manufacturing a compound represented by the formula $R^1C(OR^7)_3$
[wherein R¹ represents a $C_1$-$C_{19}$ alkyl group and R⁷ represents a $C_1$-$C_6$ alkyl group], comprising:
allowing a compound represented by the formula (15):

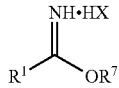

(15)

[wherein R¹ represents a $C_1$-$C_{19}$ alkyl group, R⁷ represents a $C_1$-$C_6$ alkyl group, and X represents Cl, Br, I, $HSO_4$ or $NO_3$] to react with a compound represented by the formula $R^7$—OH [wherein R⁷ represents a $C_1$-$C_6$ alkyl group] in a solvent which forms a bilayer system,

[37] the manufacturing method as described in [36], wherein the solvent which forms the bilayer system is a hydrocarbon,

[38] the manufacturing method as described in [36], wherein the solvent which forms the bilayer system is cyclohexane or methylcyclohexane,

[39] the manufacturing method as described in any one of [36] through [38], wherein R¹ is a 1-heptyl group, R⁷ is a methyl group, and X is Cl,

[40] a composition for treatment or prevention of influenza containing as active ingredient the compound or pharmacologically acceptable salts thereof as set forth in any one of [17] through [35],

[41] a compound represented by the formula (I):

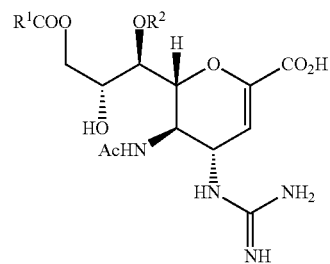

(I)

[wherein R¹ represents a alkyl group and R² represents a $C_1$-$C_4$ alkyl group], [here, the compound represented by the formula (I) may include a compound represented by the formula (II):

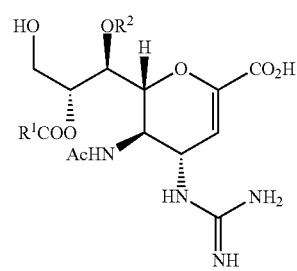

(II)

[wherein R¹ and R² have the same meanings as in the formula (I)]] having a chemical purity of 97 wt % or higher, [wherein in the case where the compound represented by the formula (II) is included, the chemical purity of the mixture of the compound represented by the formula (I) and the compound represented by the formula (II) is 97 wt % or higher], or a pharmacologically acceptable salt thereof, manufactured by a method comprising:
allowing a compound represented by the formula (13):

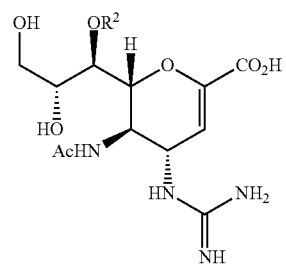

(13)

[wherein R² represents a $C_1$-$C_4$ alkyl group] to react with a compound represented by the formula $R^1C(OR^7)_3$ [wherein R¹ represents a $C_1$-$C_{19}$ alkyl group and R⁷ represents a $C_1$-$C_6$ alkyl group], or a pharmacologically acceptable salt thereof,

[42] the compound represented by the formula (I), which may include the compound represented by the formula (II), or pharmacologically acceptable salt thereof as described in [41], wherein the chemical purity is 99 wt % or higher,

[43] the compound represented by the formula (I), which may include the compound represented by the formula (II), or pharmacologically acceptable salt thereof as described in [41], wherein the chemical purity is 99.5 wt % or higher,

[44] the compound represented by the formula (I), which may include the compound represented by the formula (II), as described in any one of [41] through [43], wherein $R^1$ is a 1-heptyl group and $R^2$ is a methyl group,

[45] a compound represented by the formula (I):

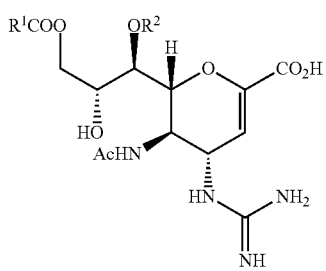
(I)

[wherein $R^1$ represents a $C_1$-$C_{19}$ alkyl group and $R^2$ represents a $C_1$-$C_4$ alkyl group], [here, the compound represented by the formula (I) may include a compound represented by the formula (II):

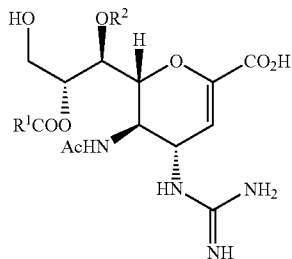
(II)

[wherein $R^1$ and $R^2$ have the same meanings as in the formula (I)]], or a pharmacologically acceptable salt thereof, containing a compound represented by the formula (VII):

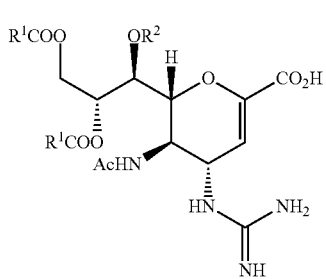
(VII)

[wherein $R^1$ and $R^2$ represent have the same meanings as in the formula (I)] in an amount of 0.5 wt % or less, manufactured by a method comprising:
allowing a compound represented by the formula (13):

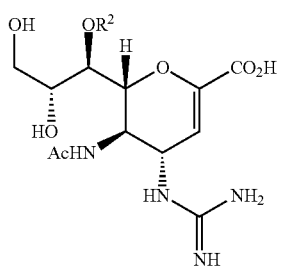
(13)

[wherein $R^2$ represents a $C_1$-$C_4$ alkyl group] to react with a compound represented by the formula $R^1C(OR^7)_3$ [wherein $R^1$ represents a $C_1$-$C_{19}$ alkyl group and $R^7$ represents a $C_1$-$C_6$ alkyl group],

[46] the compound represented by the formula (I), which may include the compound represented by the formula (II), or pharmacologically acceptable salt thereof as described in [45], containing the compound represented by the formula (VII) in an amount of 0.3 wt % or less,

[47] the compound represented by the formula (I), which may include the compound represented by the formula (II), or a pharmacologically acceptable salt thereof as described in [45], containing the compound represented by the formula (VII) in an amount of 0.1 wt % or less,

[48] the compound represented by the formula (I), which may include the compound represented by the formula (II), as described in any one of [45] through [47], wherein $R^1$ is a 1-heptyl group and $R^2$ is a methyl group,

[49] a compound represented by the formula (I):

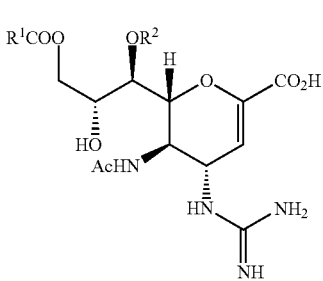
(I)

[wherein $R^1$ represents a $C_1$-$C_{19}$ alkyl group and $R^2$ represents a $C_1$-$C_4$ alkyl group], [here, the compound represented by the formula (I) may include a compound represented by the formula (II):

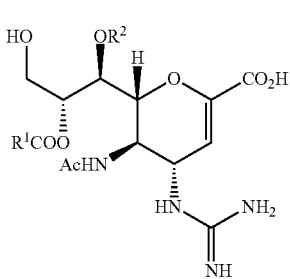
(II)

[wherein $R^1$ and $R^2$ have the same meanings as in the formula (I)]], or a pharmacologically acceptable salt thereof, containing a compound represented by the formula (VIII):

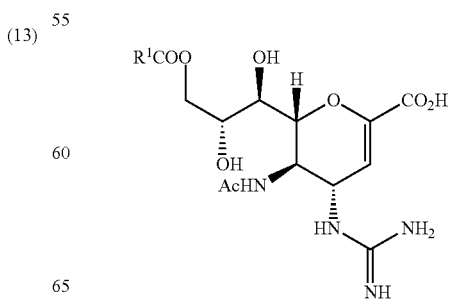
(VIII)

[wherein R¹ has the same meaning as in the formula (I)] in an amount of 0.5 wt % or less,
manufactured by a method comprising:
allowing a compound represented by the formula (13):

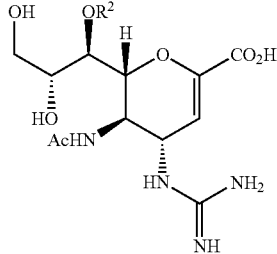
(13)

[wherein R² represents a $C_1$-$C_4$ alkyl group] to react with a compound represented by the formula $R^1C(OR^7)_3$ [wherein R¹ represents a $C_1$-$C_{19}$ alkyl group and R⁷ represents a $C_1$-$C_6$ alkyl group],

[50] the compound represented by the formula (I), which may include the compound represented by the formula (II), or pharmacologically acceptable salt thereof as described in [49], containing the compound represented by the formula (VIII) in an amount of 0.3 wt % or less,

[51] the compound represented by the formula (I), which may include the compound represented by the formula (II), or pharmacologically acceptable salt thereof as described in [49], containing the compound represented by the formula (VIII) in an amount of 0.1 wt % or less,

[52] the compound represented by the formula (II) as described in any one of [49] through [51], wherein R¹ is a 1-heptyl group and R² is a methyl group,

[53] a compound represented by the formula (I):

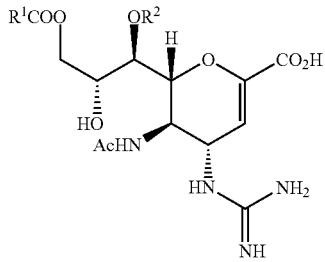
(I)

[wherein R¹ represents a $C_1$-$C_{19}$ alkyl group and R² represents a $C_1$-$C_4$ alkyl group], [here, the compound represented by the formula (I) may include a compound represented by the formula (II):

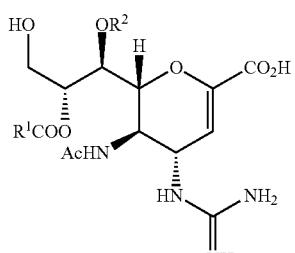
(II)

[wherein R¹ and R² have the same meanings as in the formula (I)]], or a pharmacologically acceptable salt thereof, containing an unconverted material compound represented by the formula (13):

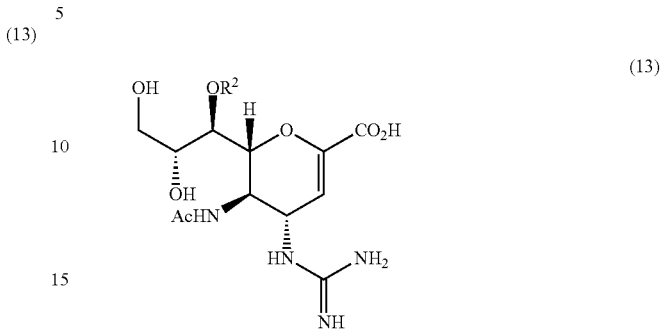
(13)

[wherein R² has the same meaning as in the formula (I)] in an amount of 0.5 wt % or less,
manufactured by a method comprising:
allowing a compound represented by the formula (13):

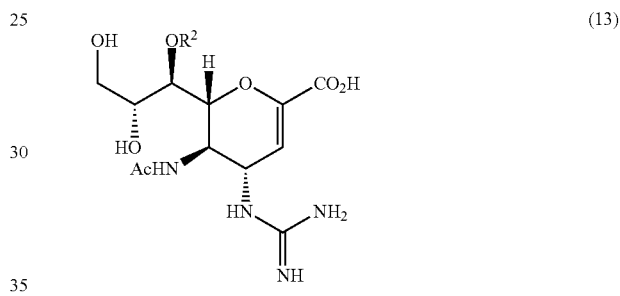
(13)

[wherein R² represents a $C_1$-$C_4$ alkyl group] to react with a compound represented by the formula $R^1C(OR^7)_3$ [wherein R¹ represents a $C_1$-$C_{19}$ alkyl group and R⁷ represents a $C_1$-$C_6$ alkyl group],

[54] the compound represented by the formula (I), which may include the compound represented by the formula (II), or pharmacologically acceptable salt thereof as described in [53], containing the compound represented by the formula (13) in an amount of 0.3 wt % or less,

[55] the compound represented by the formula (I), which may include the compound represented by the formula (II), or pharmacologically acceptable salt thereof as described in [53], containing the compound represented by the formula (13) in an amount of 0.1 wt % or less, or

[56] the compound represented by the formula (I), which may include the compound represented by the formula (II) as described in any one of [53] through [55], wherein R¹ is a 1-heptyl group and R² is a methyl group.

In the present invention, "$C_1$-$C_{19}$ alkyl group" of R¹ represents a linear or branched alkyl group having 1 to 19 carbon atoms, and may be for example, a methyl group, ethyl group, propyl group, butyl group, pentyl group, hexyl group, heptyl group, octyl group, nonyl group, decanyl group, undecanyl group, dodecanyl group, tridecanyl group, tetradecanyl group, pentadecanyl group, hexadecanyl group, heptadecanyl group, octadecanyl group or nonadecanyl group, preferably a $C_5$-$C_{19}$ alkyl group, more preferably a $C_5$-$C_{17}$ alkyl group, even more preferably a pentyl group, heptyl group, nonyl group, undecanyl group, tridecanyl group, pentadecanyl group or heptadecanyl group, further preferably a 1-pentyl group, 1-heptyl group, 1-nonyl group, 1-undecanyl group, 1-tridecanyl group, 1-pentadecanyl group or 1-heptadecanyl group, and most preferably a 1-heptyl group.

"$C_1$-$C_4$ alkyl group" of $R^2$ represents a linear or branched alkyl group having 1 to 4 carbon atoms, and may be for example, a methyl group, ethyl group, propyl group or butyl group, preferably a methyl group or ethyl group, and most preferably a methyl group.

"$C_1$-$C_6$ alkyl group" in $R^3$, $R^4$, $R^5$, $R^6$ and $R^7$ is a linear or branched alkyl group having 1 to 6 carbon atoms, and may be for example, a methyl group, ethyl group, propyl group, butyl group, pentyl group or hexyl group, preferably a $C_1$-$C_4$ alkyl group, more preferably a methyl group or ethyl group, and most preferably a methyl group.

$R^4$ and $R^5$ are preferably a hydrogen atom or a $C_1$-$C_4$ alkyl group, more preferably a methyl group or ethyl group, and most preferably a methyl group. $R^4$ and $R^5$ are preferably the same. Further, $R^4$ and $R^5$ preferably together form an oxo group.

In the present invention, "pharmacologically acceptable salt" may be, for example, a hydrohalic acid salt such as hydrofluoric acid salt, hydrochloric acid salt, hydrobromic acid salt and hydroiodic acid salt; an inorganic acid salt such as nitric acid salt, perchloric acid salt, sulfuric acid salt and phosphoric acid salt; an alkanesulfonic acid salt such as methanesulfonic acid salt, ethanesulfonic acid salt and trifluoromethanesulfonic acid salt; an arylsulfonic acid salt such as benzenesulfonic acid salt and p-toluenesulfonic acid salt; an organic acid salt such as acetic acid salt, trifluoroacetic acid salt, citric acid salt, tartaric acid salt, oxalic acid salt and maleic acid salt; an amino acid salt such as glycine salt, lysine salt, arginine salt, ornitine salt, glutamic acid salt and aspartic acid salt; an alkali metal salt such as lithium salt, sodium salt and potassium salt; an alkaline earth metal salt such as calcium salt and magnesium salt; a metal salt such as aluminum salt, iron salt, zinc salt, copper salt, nickel salt and cobalt salt; or an organic amine salt or organic ammonium salt such as ammonium salt, t-octylamine salt, dibenzylamine salt, morpholine salt, glucosamine salt, ethylenediamine salt, guanidine salt, diethylamine salt, triethylamine salt, dicyclohexylamine salt, procain salt, ethanolamine salt, diethanolamine salt, piperazine salt and tetramethylammonium salt, preferably a hydrohalic acid salt or organic acid salt, and more preferably trifluoroacetic acid salt.

When the compounds of the present invention are exposed to the atmosphere or are blended with water or organic solvent, they may form hydrates or solvates. Such hydrates and solvates are also embraced in the compounds of the present invention. Compound (Ib) and compound (IIb) include an anhydride and hydrates. Preferably, the hydrate of compound (Ib) and hydrate of compound (IIb) are monohydrates.

The compounds of the present invention have an asymmetric carbon atom within their molecule, and thus there exist stereoisomers (enantiomers and diastereomers are included). These stereoisomers and mixtures thereof in an arbitrary ratio (including racemic form) are embraced in the compounds of the present invention.

It is known that when compound (I) is administered to a warm-blooded animal, the acyloxy group at the 3-position of the side chain is converted into a hydroxyl group by a metabolic reaction such as hydrolysis, and the generated compound (III) shows pharmacological activity (Patent Document 1 and the like). In addition, when compound (II) is administered to a warm-blooded animal, the acyloxy group at the 2-position of the side chain is converted into a hydroxyl group by a metabolic reaction such as hydrolysis, and compound (III) is generated in a similar manner. Since both compound (I) and compound (II) are converted into the same compound (III), which is an active metabolite, within an organism of a warm-blooded animal, it can be considered that both the compounds are active ingredients, from the point of view of using a mixture of compound (I) and compound (II) as a medicament. On the other hand, since a medicament is required to show a constant pharmacological effect and physical and chemical stability, it is preferable that the composition ratio of these compounds is constant, from the point of view of the quality of a mixture of compound (I) and compound (II) as a medicament.

In the present invention, the chemical purity of the compound, the content of a compound as an impurity, or the composition ratio of a mixture of compound (I) and compound (II) may be determined by methods known in the field of organic chemistry (for example, high performance liquid chromatography, weight %, and the like), and is preferably determined by peak area ratios under high performance liquid chromatography (hereinafter also referred to as HPLC). The measurement conditions for HPLC shall be selected appropriately; however, they are preferably as shown hereinbelow.

HPLC measurement conditions (1)
Column: L-column ODS (4.6 mmID×25 cm, particle diameter 5 μm, manufactured by Chemicals Evaluation and Research Institute)
Column temperature: 30° C.
Measurement wavelength: 210 nm
Mobile phase:
 A: 0.1% PIC B-7 (Low UV, manufactured by Waters Corporation) aqueous solution/acetonitrile (9/1, v/v)
 B: 0.1 mol/l phosphate buffer solution (pH 3.0)/acetonitrile (7/3, v/v)
[Here, 0.1 mol/l phosphate buffer solution (pH 3.0) is a buffer solution prepared by adding 0.1 mol/l phosphoric acid to 0.1 mol/l aqueous potassium dihydrogen phosphate solution to adjust its pH to 3.0.]
Gradient Conditions:

| Time (min.) | Mobile phase A (%) | Mobile phase B (%) |
|---|---|---|
| 0-3 | 100 | 0 |
| 3-23 | 100→0 | 0→100 |
| 23-90 | 0 | 100 |

Flow rate: 1 ml/min
Sample concentration: approximately 1 g/l
Injection amount: 20 μl
Range detected with peak: from 0 minute to approximately 1.2 times the length of retention time of compound (I)
HPLC measurement conditions (2)
Column: L-column ODS (4.6 mmID×25 cm, particle diameter 5 μm, manufactured by Chemicals Evaluation and Research Institute)
Column temperature: 30° C.
Measurement wavelength: 210 nm
Mobile phase:
 0.1 mol/l phosphate buffer solution (pH 3.0)/acetonitrile (23/17, v/v)
[Here, 0.1 mol/l phosphate buffer solution (pH 3.0) is a buffer solution prepared by adding 0.1 mol/l phosphoric acid to 0.1 mol/l aqueous potassium dihydrogen phosphate solution to adjust its pH to 3.0.]
Flow rate: 1 ml/min
Sample concentration: approximately 1 g/l
Injection amount: 20 μl Range detected with peak: from approximately 1.2 times to 18 times the length of retention time of compound (I)

By HPLC measurement conditions (1), the peak area ratios of compound (I), compound (II), and compound as impurity, which are detected from 0 minute to approximately 1.2 times the length of retention time of compound (I), are measured. By HPLC measurement conditions (2), the peak area ratio of compound as impurity, which is detected from approximately 1.2 times to 18 times of the length of retention time of compound (I), is measured. Here, the peaks of the compounds as impurities represent the peaks when the peak of compound (I), the peak of compound (II), and the peaks detected when solvent alone is injected [for example, the peak of solvent and the peak derived from noise], are subtracted from all of the peaks that are detected as 0.01% or more.

The chemical purity (%) of compound (I) can be calculated according to the following equation.

Chemical purity of compound(I)=100−sum of peak area ratio(%) of compound as impurity Compound (I) may include compound (II), and in the case where compound (I) includes compound (II), the chemical purity is calculated as the mixture of compound (I) and compound (II).

The content of compound (VII) can be calculated as the peak area ratio under HPLC measurement conditions (2). The content of compound (VIII) and compound (13) can be calculated as the peak area ratio under HPLC measurement conditions (1).

The peak area ratios of compound (I) and compound (II) can be measured in accordance with the aforementioned HPLC measurement conditions (1). The composition ratio (%) of a mixture of compound (I) and compound (II) can be calculated from the following equation.

Composition ratio of compound(I)=[peak area ratio of compound(I)/[peak area ratio of compound(I)+ peak area ratio of compound(II)]]×100

Composition ratio of compound(II)=[peak area ratio of compound(II)/[peak area ratio of compound (I)+peak area ratio of compound(II)]]×100

The chemical purity of compound (I) or pharmacologically acceptable salt thereof is preferably 95% or more, more preferably 97% or more, even more preferably 98% or more, further preferably 99% or more, and most preferably 99.5% or more, by weight. Compound (I) may contain compound (II), and in the case where compound (I) contains compounds (II), the chemical purity is calculated by taking both compound (I) and compound (II) as active ingredients. It is more preferable that the content of compounds other than compound (I) [and compound (II)] or pharmacologically acceptable salt thereof is below the detection limit.

Concerning compound (I) which may contain compound (II), the composition ratio of compound (I) and compound (II) is preferably 85:15 to 100:0, more preferably 90:10 to 100:0, even more preferably 92:8 to 100:0, and most preferably 95:5 to 100:0, by weight. The content of a compound represented by formula (II) may be below the detection limit.

Concerning compound (I) or pharmacologically acceptable salt thereof, the content of compound (VII) is preferably 2% or less, more preferably 1% or less, even more preferably 0.5% or less, further preferably 0.3% or less, and most preferably 0.1% or less, by weight. It is more preferable that the content of compound (VII) is below the detection limit.

Concerning compound (I) or pharmacologically acceptable salt thereof, the content of compound (VIII) is preferably 2% or less, more preferably 1% or less, even more preferably 0.5% or less, further preferably 0.3% or less, and most preferably 0.1% or less, by weight. It is more preferable that the content of compound (VIII) is below the detection limit.

Concerning compound (I) or pharmacologically acceptable salt thereof, the content of compound (13) is preferably 2% or less, more preferably 1% or less, even more preferably 0.5% or less, further preferably 0.3% or less, and most preferably 0.1% or less, by weight. It is more preferable that the content of compound (13) is below the detection limit.

The present invention shown by Process A is superior to publicly known manufacturing methods or synthetic intermediates, in points given below, for example.

(i) Concerning the production procedures of compound (IVb) of Process W and compound (VIb) of Process Z, since an acetamide group exists in their starting materials compound (IVa) and compound (VIa), N-methylation occurs as a side reaction. For example, with respect to compound (VIa), the N-methylated compound is generated at approximately 12% (refer to data of N-methylated compound of compound (Via) described in Comparative Example 1).

In contrast, compound (7) has no functional group which may be methylated other than the hydroxyl group at the 1-position of the side chain, and thus N-methylation as a side reaction does not occur in the methylation reaction of compound (7). In addition, the oxazolidine ring of compound (7) simultaneously serves as a protective group to prevent N-methylation and as a partial structure which is to be converted into an acetamide group at the 5-position in Step A-6. Further, since compound (7) is a crystalline solid, it can easily be purified by recrystallization. Therefore, compound (7) contributes to the improvement of the overall yield in Process A, by achieving efficient methylation of the hydroxyl group at the 1-position of the side chain, and by achieving a reduction in the number of procedures in Process A.

(ii) Concerning the production procedure of compound (IVg) in Process W, Process Y, and Process Z, since the reaction is carried out under a high temperature of 80° C. or higher using approximately 6 moles of sodium azide, it is extremely hazardous especially from an industrial perspective, when the explosive nature of azide compounds is taken into consideration. In addition, the stereoselectivity of the reaction at the 4-position is not enough, and thus the generation ratio of compound (IVg) and the undesired stereoisomer in which the azide group has the opposite configuration of compound (IVg), is approximately 7:1 (refer to Comparative Example 2).

In contrast, concerning the azidation reaction of compound (8), by using a Lewis acid, the amount of azidation agent used is reduced to approximately 1.5 to 2 equivalents, and the reaction proceeds under extremely mild conditions of 0° C. to 30° C. In addition, the stereoselectivity of the reaction at the 4-position is improved, and thus the generation ratio of compound (9) and the undesired stereoisomer is improved to 15:1 (refer to data described in Step A-6 of Example 1).

Accordingly, the manufacturing method of compound (9) from compound (8) improves the practicality of Process A from an industrial perspective, by achieving an improvement in the safety of the azidation reaction and stereoselective production of the desired isomer.

(iii) Compound (IIIa) in Process Y and Process Z is a salt of trifluoroacetic acid which is corrosive, and is an amorphous solid, therefore being unable to be easily purified by recrystallization.

In contrast, compound (13) is produced from compound (12), by a reaction with only water under mild conditions. In addition, since compound (13) is a crystalline solid, it can easily be purified by recrystallization. From an industrial perspective, it is extremely important to use a starting material with a purity as high as possible in the final procedure of the production, in order to obtain the desired compound with high purity. Therefore, compound (13) contributes to the production of compound (I) with high purity, by providing a starting material with high purity in the final procedure.

(iv) Concerning the production procedure of compound (IVk) and compound (Ia) in Process W, (a) protection of a carboxyl group is necessary, (b) a 2,3-diacylated compound is generated as by-product, and (c) purification by silica gel column chromatography is required to remove the octanoic acid derived from the reagent. Here, as an acylation reaction of a hydroxyl group using an ortho ester, the following reaction is known (Carbohydrate Research, 1987, Vol. 167, pp. 77-86). $R^a$ represents a $C_1$-$C_4$ alkyl group and the like. In the following reaction, the reactive functional group is a hydroxyl group only.

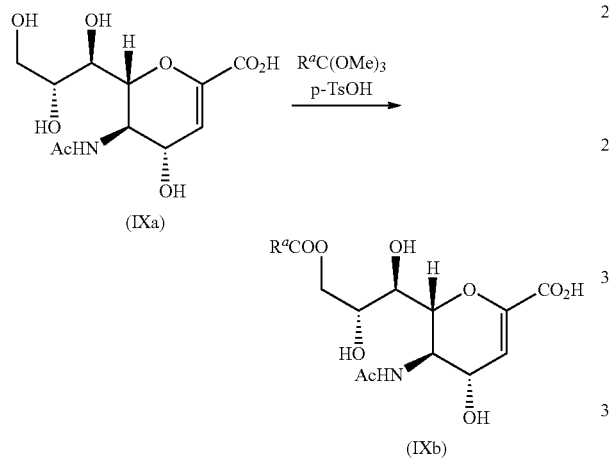

In contrast, no similar acylation reaction that proceeds in the presence of a nitrogen, functional group (guanidyl group), which is considered to be more reactive, is known. In the production procedure of compound (I) from compound (13), an acylation reaction proceeds with a fine yield in the presence of a guanidyl group. In the present procedure, (a') protection of a carboxyl group is unnecessary, (b') selective mono-acylation proceeds, resulting in scarce generation of a 2,3-diacylated compound as a by-product and (c') removal of by-product derived from the reagent by silica gel column chromatography is not required. Therefore, the manufacturing method of compound (I) from compound (13) contributes largely to the production of compound (I) with high purity.

(v) An acylation reaction of a hydroxyl group using an imino ester is not known to present date. The production procedure of compound (I) from compound (13) can also be conducted by using an imino ester compound (15) and a compound represented by the formula $R^7$—OH, in place of an ortho ester compound (14). The production of compound (14) by a conventional method is very low in yield [refer to (vii) given below]. By using compound (15) directly, the inefficient production procedure of compound (14) from compound (15) can be omitted.

(vi) Concerning the production procedure of compound (IVk) and compound (Ia) in Process W, compound (VII), which is a 2,3-diacylated compound, is generated as a by-product. Accordingly, a reduction in the amount of compound (VII) contained is required to obtain compound (Ia) with high purity (refer to Comparative Example 3).

In the production procedure of compound (I) from compound (13), selective monoacylation reaction can be achieved by using compound (14) or compound (15), and thus compound (I) in which the amount of compound (VII) contained is less to such an extent as to be practical, can be produced (refer to Step A-10 of Example 1).

Therefore, the manufacturing method of compound (I) from compound (13) contributes largely to the production of compound (I) with high purity.

(vii) In the production of compound (14), when a compound represented by the formula $R^7$—OH is used as a reagent and as a solvent to react with compound (15), following a publicly known method (Journal of American Chemical Society, 1942, vol. 64, pp. 1825-1827), the yield of compound (14) is approximately 35% to 50% (refer to Comparative Example 4).

In contrast, when compound (15) is allowed to react with a compound represented by the formula $R^7$—OH in a solvent which forms a bilayer system, the yield of compound (14) is improved remarkably to approximately 80% to 85% (refer to Example 9). Therefore, the manufacturing method of compound (14) from compound (15) contributes to the improvement of the overall yield of Process A, by providing an efficient method of manufacturing compound (14), which is used in the production of compound (I).

Effect of the Invention

The novel method of manufacturing neuraminic acid derivatives via the novel synthetic intermediate according to the present invention is superior from an industrial perspective, compared with publicly known manufacturing methods. In addition, neuraminic acid derivatives with high purity can be obtained in high yield by the present manufacturing method.

DETAILED DESCRIPTION OF THE PREFERRED EMBODIMENTS

In the present invention, the method of manufacturing neuraminic acid derivatives can be conducted in accordance with the following Process A through Process G.

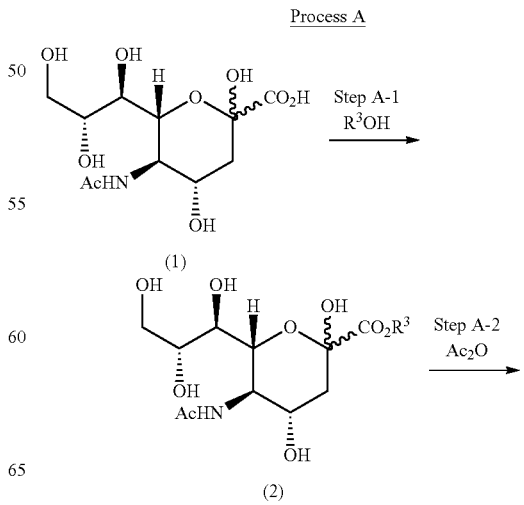

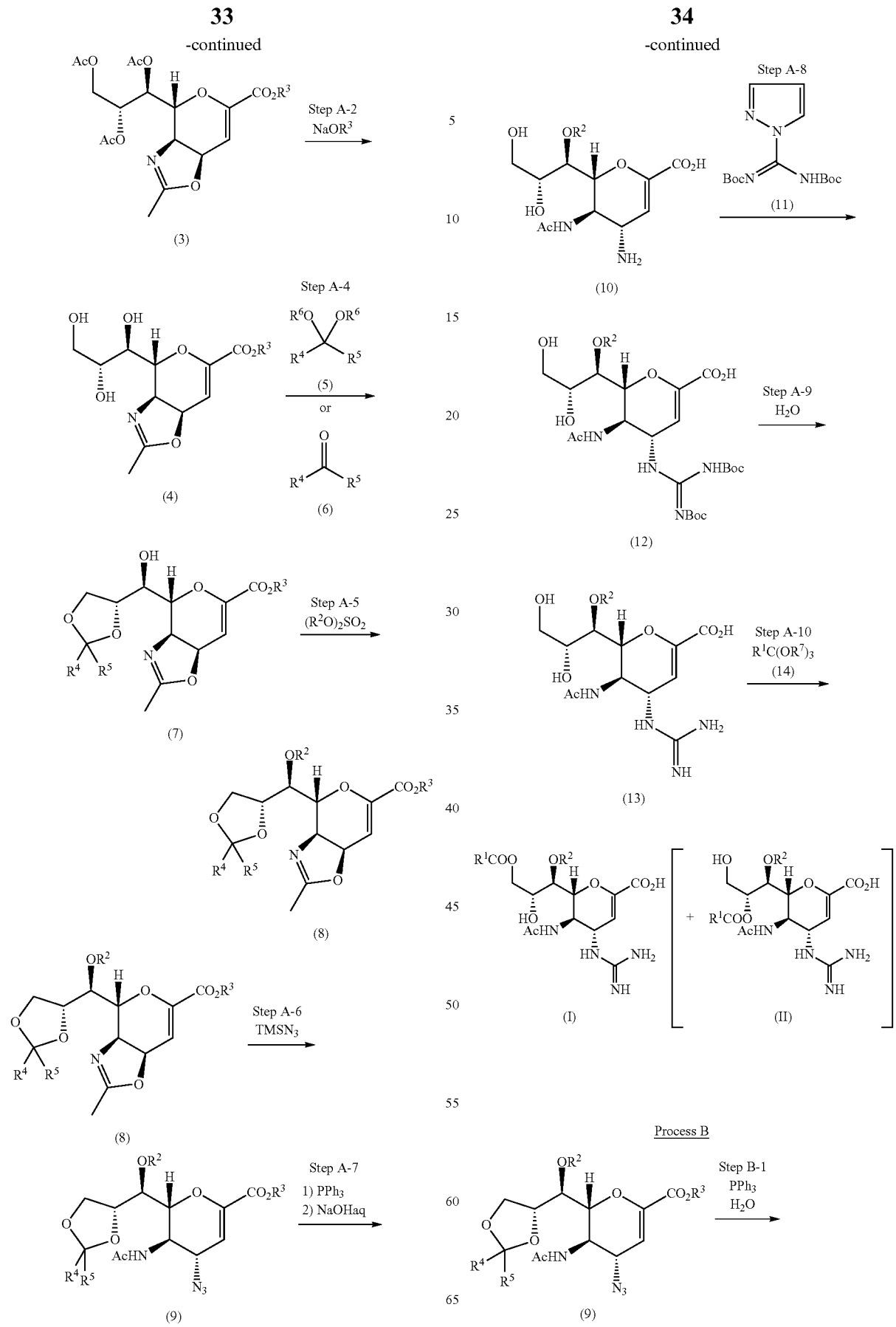

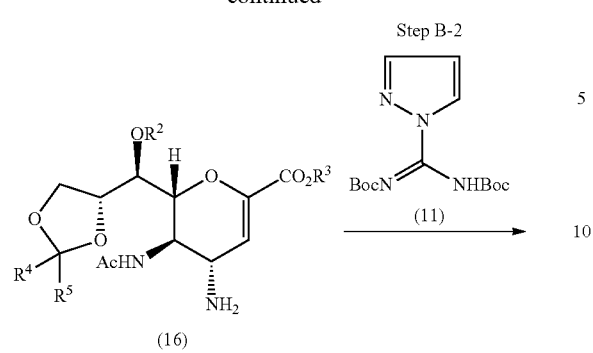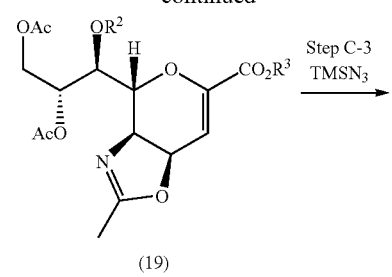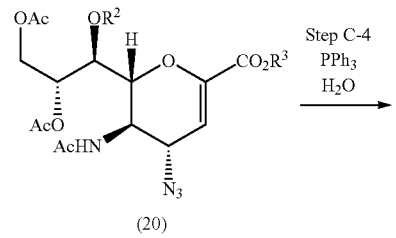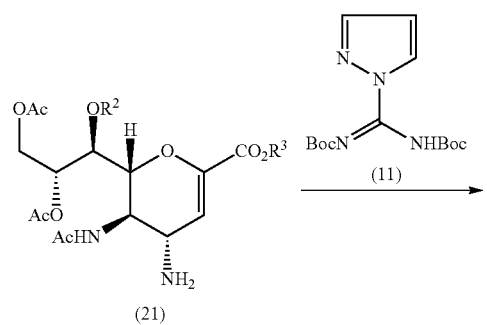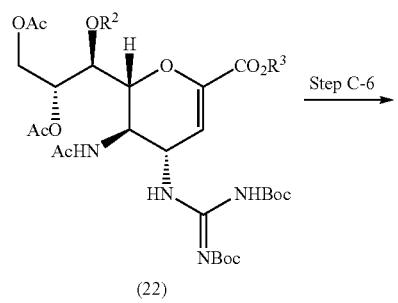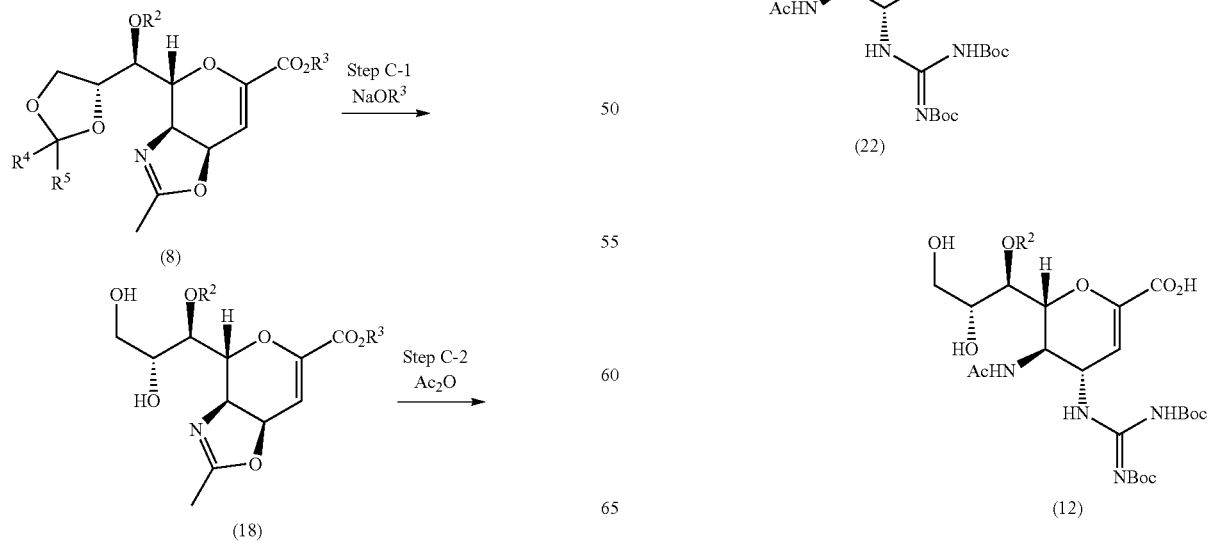

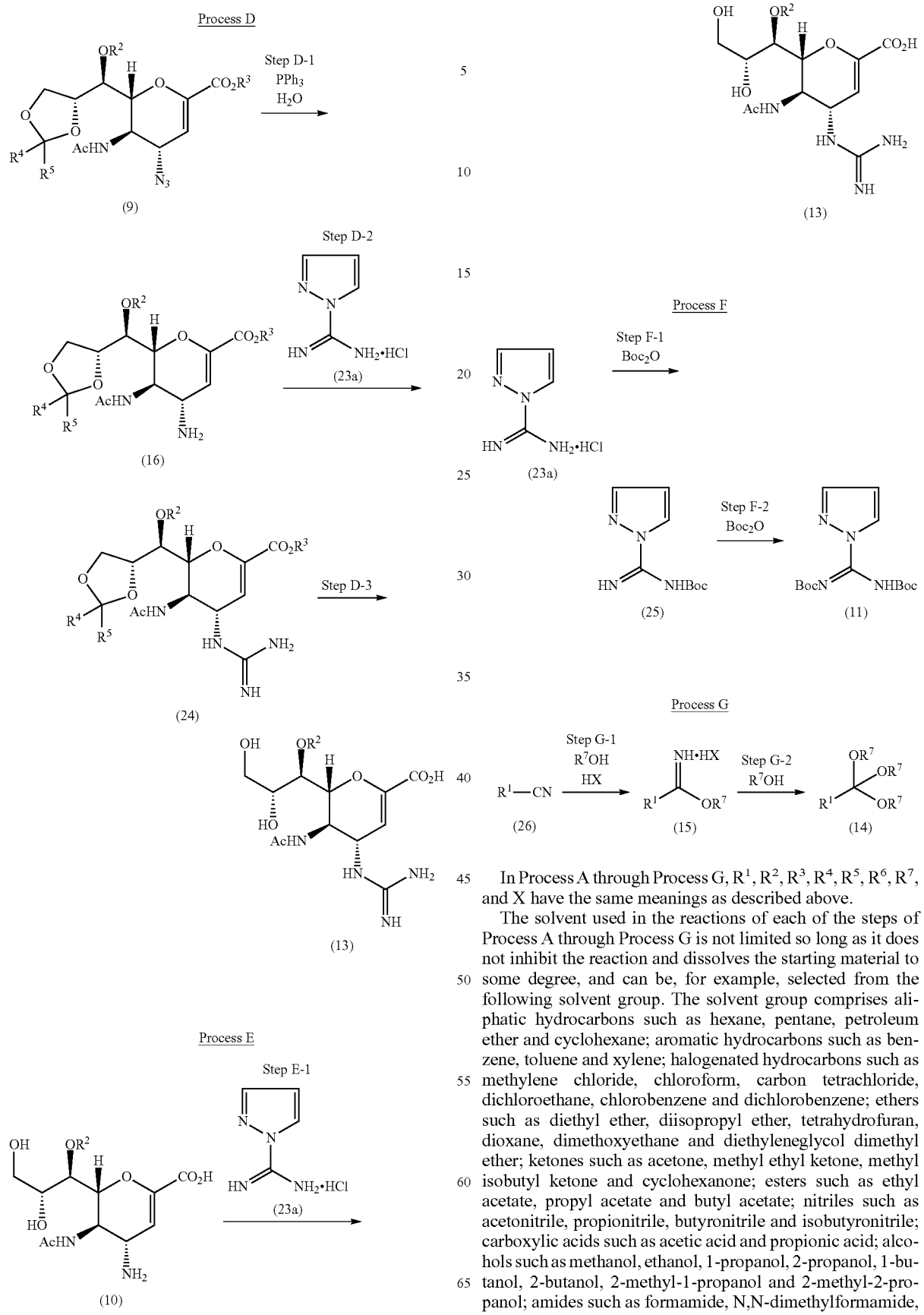

In Process A through Process G, $R^1$, $R^2$, $R^3$, $R^4$, $R^5$, $R^6$, $R^7$, and X have the same meanings as described above.

The solvent used in the reactions of each of the steps of Process A through Process G is not limited so long as it does not inhibit the reaction and dissolves the starting material to some degree, and can be, for example, selected from the following solvent group. The solvent group comprises aliphatic hydrocarbons such as hexane, pentane, petroleum ether and cyclohexane; aromatic hydrocarbons such as benzene, toluene and xylene; halogenated hydrocarbons such as methylene chloride, chloroform, carbon tetrachloride, dichloroethane, chlorobenzene and dichlorobenzene; ethers such as diethyl ether, diisopropyl ether, tetrahydrofuran, dioxane, dimethoxyethane and diethyleneglycol dimethyl ether; ketones such as acetone, methyl ethyl ketone, methyl isobutyl ketone and cyclohexanone; esters such as ethyl acetate, propyl acetate and butyl acetate; nitriles such as acetonitrile, propionitrile, butyronitrile and isobutyronitrile; carboxylic acids such as acetic acid and propionic acid; alcohols such as methanol, ethanol, 1-propanol, 2-propanol, 1-butanol, 2-butanol, 2-methyl-1-propanol and 2-methyl-2-propanol; amides such as formamide, N,N-dimethylformamide, N,N-dimethylacetamide, N-methyl-2-pyrrolidone and hexamethylphosphoroamide; sulfoxides such as dimethyl sulfoxide; sulfones such as sulforane; water; and mixtures thereof.

In the reactions of each of the steps of Process A through Process G, the reaction temperature differs depending on solvent, starting material, reagent and the like, and is selected appropriately. In addition, the reaction time differs depending on solvent, starting material, reagent and the like, and is selected appropriately.

In the reactions of each of the steps of Process A through Process G, the desired compound of each of the steps can be isolated from a reaction mixture in accordance with ordinary methods after completion of the reaction. The desired compound may be obtained by, for example, (i) removing insoluble matters such as catalyst as necessary, (ii) extracting the desired compound by adding water and solvent which is immiscible with water (for example, ethyl acetate and the like) to the reaction mixture, (iii) washing the organic layer with water and drying it as necessary by using a drying agent such as anhydrous magnesium sulfate, and (iv) distilling off the solvent. The obtained desired compound can be further purified as necessary, by ordinary methods (for example, recrystallization, reprecipitation, or silicagel column chromatography). In addition, the desired compound of each procedure can also be used in the subsequent reaction without purification.

(Process A)

Process A shows a method of manufacturing a compound represented by the formula (I) [which may include a compound represented by the formula (II)] or a pharmacologically acceptable salt thereof.

(Step A-1)

Step A-1 is a procedure to allow publicly known compound (1) to react with an alcohol represented by the formula $R^3OH$ in the presence of acid, to produce compound (2). The alcohol represented by the formula $R^3OH$ are either publicly known, or can easily be produced from a publicly known compound, and is preferably methanol.

The acid used is not limited so long as it is used for esterification of a carboxyl group using an alcohol, and may be for example, an organic acid such as acetic acid, propionic acid, trifluoroacetic acid and pentafluoropropionic acid, an organic sulfonic acid such as p-toluenesulfonic acid, camphorsulfonic acid and trifluoromethanesulfonic acid, or an inorganic acid such as hydrogen chloride, hydrogen bromide, hydrogen iodide, phosphoric acid, sulfuric acid and nitric acid, preferably an inorganic acid, and most preferably sulfuric acid.

In Step A-1, a compound represented by the formula $HC(OR^3)_3$ may be used to accelerate the reaction. The compound represented by the formula $HC(OR^3)_3$ is either publicly known, or can easily be produced from a publicly known compound. The compound represented by the formula $HC(OR^3)_3$ is preferably trimethyl orthoformate [$HC(OMe)_3$]. $R^3$ in the compound represented by the formula $HC(OR^3)_3$ is preferably the same as $R^3$ in the alcohol represented by the formula $R^3OH$.

The solvent used is preferably an aromatic hydrocarbon, a halogenated hydrocarbon, an ether or an alcohol represented by the formula $R^3OH$, more preferably an alcohol represented by the formula $R^3OH$, and most preferably methanol.

The reaction temperature is preferably −20° C. to 100° C., and more preferably 20° C. to 60° C.

The reaction time is preferably 30 minutes to 40 hours, and more preferably 1 to 10 hours.

(Step A-2)

Step A-2 is a procedure to allow compound (2) to react with acetic acid anhydride in the presence of acid, to produce compound (3).

The acid used is not limited so long as it promotes formation of a carbon-carbon double bond by acetic acid elimination at the 2- and 3-positions of the tetrahydropyrane ring, formation of an oxazoline ring at the 4- and 5-positions of the tetrahydropyrane ring, and acetylation of the hydroxyl group at the 1-, 2-, and 3-positions of the side chain. For example, it may be an organic acid such as acetic acid, propionic acid, trifluoroacetic acid and pentafluoropropionic acid, an organic sulfonic acid such as p-toluenesulfonic acid, camphorsulfonic acid and trifluoromethanesulfonic acid, or an inorganic acid such as hydrogen chloride, hydrogen bromide, hydrogen iodide, phosphoric acid, sulfuric acid and nitric acid, preferably an inorganic acid, and most preferably sulfuric acid.

The solvent used is preferably a hydrocarbon, and most preferably 1-heptane. It is also preferable that Step A-2 is conducted in the absence of solvent.

The reaction temperature is preferably −20° C. to 100° C., and more preferably 0° C. to 60° C.

The reaction time is preferably 30 minutes to 60 hours, and more preferably 1 to 20 hours.

(Step A-3)

Step A-3 is a procedure to allow compound (3) to react with a compound represented by the formula $NaOR^3$, to produce compound (4).

In Step A-3, the compound represented by the formula $NaOR^3$ is preferably sodium methoxide or sodium ethoxide, and most preferably sodium methoxide. In Step A-3, a compound represented by the formula $LiOR^3$ or $KOR^3$ may be used instead of the compound represented by the formula $NaOR^3$. $R^3$ in the compound represented by the formula $NaOR^3$, $LiOR^3$ or $KOR^3$ is preferably the same as $R^3$ of compound (3).

The solvent used is preferably an alcohol, more preferably methanol or ethanol, and most preferably methanol. The solvent used is preferably an alcohol represented by the formula $R^3OH$ [wherein $R^3$ is the same as $R^3$ of the compound represented by the formula $NaOR^3$].

The reaction temperature is preferably −20° C. to 70° C., and more preferably 0° C. to 50° C.

The reaction time is preferably 1 minute to 5 hours, and more preferably 5 minutes to 1 hour.

(Step A-4)

Step A-4 is a procedure to allow compound (4) to react with compound (5) or compound (6), to produce compound (7). Compound (5) or compound (6) is either publicly known, or can easily be produced from a publicly known compound.

In Step A-4, of compound (5) and compound (6), compound (5) is preferably used, more preferably dimethyl carbonate [$(MeO)_2CO$] or diethyl carbonate, and most preferably dimethyl carbonate.

In Step A-4, in the case where compound [$(R^6O)_2CO$], in which $R^4$ and $R^5$ of compound (5) together form an oxo group, is used, a base may be further used, preferably. Such base is not limited so long as it is used for conversion of 1,2-diol into cyclic carbonate, and may be for example, an alkali metal carbonate such as lithium carbonate, sodium carbonate, potassium carbonate and cesium carbonate; an alkali metal hydrogencarbonate such as lithium hydrogencarbonate, sodium hydrogencarbonate and potassium hydrogencarbonate; an alkali metal hydroxide such as lithium hydroxide, sodium hydroxide and potassium hydroxide; an alkaline earth metal hydroxide such as calcium hydroxide and barium hydroxide; an alkali metal hydride such as lithium hydride, sodium hydride and potassium hydride; an alkali metal amide such as lithium amide, sodium amide and potassium amide; an alkali metal alkoxide such as lithium methoxide, sodium methoxide, sodium ethoxide, sodium tert-butoxide and potassium tert-butoxide; a lithium alkyl amide such as lithium diisopropylamide; a lithium silyl amide such as lithium bistrimethylsilyl amide and sodium bistrimethylsilyl amide; or an organic amine such as triethylamine, tributylamine, N,N-diisopropylethylamine, N-methylpiperidine, N-methylmorpholine, N-ethylmorpholine, pyridine, picoline, 4-dimethylaminopyridine, 4-pyrrolidinopyridine, 2,6-di(tert-butyl)-4-methylpyridine, quinoline, N,N-dimethylaniline, N,N-diethylaniline, 1,5-diazabicyclo[4,3,0]non-5-ene (DBN), 1,4-diazabicyclo[2,2,2]octane (DABCO), 1,8-diazabicyclo[5,4,0]undec-7-ene (DBU); preferably an alkali metal carbonate, an alkali metal alkoxide or an alkali metal hydride, more preferably an alkali metal alkoxide, and most preferably sodium methoxide.

In Step A-4, in the case where compound (5) [except for a compound represented by the formula $(R^6O)_2CO$] or compound (6) is used, an acid may be further used, preferably. Such acid is not limited so long as it is used for conversion of 1,2-diol into cyclic acetal or cyclic ketal, and may be for example, an organic acid such as acetic acid, propionic acid, trifluoroacetic acid and pentafluoropropionic acid, an organic sulfonic acid such as p-toluenesulfonic acid, camphorsulfonic acid and trifluoromethanesulfonic acid, or an inorganic acid such as hydrogen chloride, hydrogen bromide, hydrogen iodide, phosphoric acid, sulfuric acid and nitric acid.

In Step A-4, in the case where compound [$(R^6O)_2CO$], in which $R^4$ and $R^5$ of compound (5) together form an oxo group, is used, the solvent used is preferably an alcohol, more preferably methanol or ethanol, and most preferably methanol. In the case where compound (5) is used, the solvent used is preferably an alcohol represented by the formula $R^6OH$ [wherein $R^6$ is the same as $R^6$ of compound (5)]. In addition, the solvent used is preferably an alcohol represented by the formula $R^6OH$ [wherein $R^6$ is the same as $R^6$ of compound (5)].

In Step A-4, in the case where compound (5) [except for a compound represented by the formula $(R^6O)_2CO$] or compound (6) is used, the solvent used is preferably a halogenated hydrocarbon, an amide, or a ketone, more preferably a ketone, and most preferably acetone. In a case where compound (5) [except for a compound represented by the formula $(R^6O)_2CO$] is used and the solvent used is a ketone, the solvent is preferably a ketone represented by the formula (6).

The reaction temperature is preferably −30° C. to 80° C., and more preferably 0° C. to 50° C.

The reaction time is preferably 30 minutes to 60 hours, and more preferably 1 to 20 hours.

(Step A-5)

Step A-5 is a procedure to allow compound (7) to react with a compound represented by the formula $(R^2O)_2SO_2$ in the presence of a base, to produce compound (8). The compound represented by the formula $(R^2O)_2SO_2$ is either publicly known, or can easily be produced from a publicly known compound.

In Step A-5, the compound represented by the formula $(R^2O)_2SO_2$ is preferably dimethyl sulfuric acid [$(MeO)_2SO_2$].

The base used is not limited so long as it is used for alkylation of a hydroxyl group, and may be, for example, a base indicated in Step A-4, preferably an alkali metal hydride, and most preferably sodium hydride.

The solvent used is preferably an ether, an amide, or a mixture thereof, more preferably tetrahydrofuran, N,N-dimethylacetamide, or a mixture thereof, and most preferably a mixture of tetrahydrofuran and N,N-dimethylacetamide.

The reaction temperature is preferably −50° C. to 80° C., and more preferably −20° C. to 50° C.

The reaction time is preferably 10 minutes to 20 hours, and more preferably 30 minutes to 10 hours.

(Step A-6)

Step A-6 is a procedure to allow compound (8) to react with trimethylsilyl azide in the presence of a Lewis acid, to produce compound (9).

The Lewis acid used is not limited so long as it promotes azidation which is accompanied by ring opening of an oxazolidine ring, and may be for example, a zinc halide such as zinc chloride and zinc bromide; a boron trihalide such as boron trifluoride, boron trichloride and boron tribromide, and their complexes with ethers or thioethers; a titanium (IV) alkoxide such as titanium (IV) methoxide, titanium (IV) ethoxide, titanium (IV) propoxide, titanium (IV) isopropoxide, titanium (IV) butoxide and titanium (IV) 2-ethylhexoxide; a zirconium (IV) alkoxide such as zirconium (IV) ethoxide, zirconium (IV) propoxide, zirconium (IV) isopropoxide isopropanol complex, zirconium (IV) butoxide and zirconium (IV) tert-butoxide; a scandium (III) alkoxide such as scandium (III) isopropoxide; a scandium salt such as scandium trifluoromethanesulfonate; a yttrium (III) alkoxide such as yttrium (III) isopropoxide; a yttrium salt such as yttrium trifluoromethanesulfonate; a lanthanoid isopropoxide such as gadolinium (III) isopropoxide, dysprosium (III) isopropoxide, ytterbium (III) isopropoxide and erbium (III) isopropoxide; an aluminum alkoxide such as aluminum ethoxide, aluminum butoxide, aluminum sec-butoxide and aluminum tert-butoxide; preferably a titanium (IV) alkoxide, and most preferably titanium (IV) isopropoxide.

The solvent used is preferably an aromatic hydrocarbon, an alcohol, or a mixture thereof, more preferably 2-propanol, 2-methyl-2-propanol, toluene or a mixture thereof, and most preferably a mixture of 2-methyl-2-propanol and toluene.

The reaction temperature is preferably −20° C. to 60° C., and more preferably 0° C. to 30° C.

The reaction time is preferably 1 to 100 hours, and more preferably 5 to 30 hours.

(Step A-7)

Step A-7 comprises (Step A-7a), a procedure to treat compound (9) with triphenylphosphine; and (Step A-7b), a procedure to treat the compound obtained in Step A-7a with a base and water.

(Step A-7a)

The solvent used is preferably an ether or an ester, more preferably tetrahydrofuran or ethyl acetate, and most preferably tetrahydrofuran.

The reaction temperature is preferably −30° C. to 100° C., and more preferably 0° C. to 70° C.

The reaction time is preferably 1 minute to 20 hours, and more preferably 5 minutes to 5 hours.

(Step A-7b)

The base used is not limited so long as it promotes hydrolysis of an ester group and elimination of a cyclic carbonate group, and may be for example, an alkali metal carbonate such as lithium carbonate, sodium carbonate, potassium carbonate and cesium carbonate; an alkali metal hydrogencarbonate such as lithium hydrogencarbonate, sodium hydrogencarbonate and potassium hydrogencarbonate; an alkali metal hydroxide such as lithium hydroxide, sodium hydroxide and potassium hydroxide; or an alkaline earth metal hydroxide such as calcium hydroxide and barium hydroxide, preferably an alkali metal hydroxide, more preferably sodium hydroxide or potassium hydroxide, and most preferably sodium hydroxide.

The solvent used is preferably an ether or an alcohol, more preferably tetrahydrofuran, methanol or ethanol, and most preferably tetrahydrofuran.

The reaction temperature is preferably −30° C. to 100° C., and more preferably 0° C. to 70° C.

The reaction time is preferably 10 minutes to 20 hours, and more preferably 30 minutes to 10 hours.

In the case where a protective group of 1,2-diol of compound (9) is a cyclic acetal or cyclic ketal, deprotection of the 1,2-diol protective group is conducted by treating the compound obtained in Step A-7a with a base and water, and then adjusting the pH of the reaction mixture to acidic.

(Step A-8)

Step A-8 is a procedure to allow compound (10) to react with compound (11), to produce compound (12). Compound (11) can be produced in accordance with Process F.

The solvent used is preferably water, an amide, a ketone, a nitrile, an alcohol or a mixture thereof, more preferably a mixture of water and an alcohol, and most preferably a mixture of water and methanol.

The reaction temperature is preferably −30° C. to 80° C., and more preferably 0° C. to 50° C.

The reaction time is preferably 1 to 160 hours, and more preferably 5 to 80 hours.

(Step A-9)

Step A-9 is a procedure to allow compound (12) to react with water to produce compound (13).

The solvent used is preferably an alcohol, water, or a mixture thereof, more preferably methanol, water, or a mixture thereof, and most preferably water.

The reaction temperature is preferably 0° C. to 160° C., and more preferably 50° C. to 110° C.

The reaction time is preferably 30 minutes to 20 hours, and more preferably 1 to 10 hours.

In Step A-8 and Step A-9, compound (13) can be produced also by reacting compound (10) with a compound represented by the formula (23):

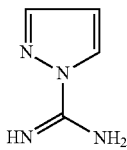

(23)

or a salt thereof. Compound (23) or a salt thereof is either publicly known, or can easily be produced from a publicly known compound.

In the present step, compound (23) or a salt thereof is preferably the hydrochloride of compound (23). In this step, a base (preferably an organic amine or an alkali metal hydroxide, and more preferably an alkali metal hydroxide) may be further used for the purpose of controlling the pH during the reaction.

The solvent used is preferably an alcohol, water, or a mixture thereof, and most preferably a mixture of methanol and water.

The reaction temperature is preferably −20° C. to 70° C., and more preferably 0° C. to 50° C.

The reaction time is preferably 1 to 200 hours, and more preferably 10 to 100 hours.

The pH during the reaction is preferably 7 to 10, and more preferably 7 to 9.

(Step A-10)

Step A-10 is a procedure to allow compound (13) to react with compound (14) in the presence of acid to produce compound (I) [which may contain a compound represented by the formula (II)]. Compound (14) can be produced in accordance with Process G.

In Step A-10, compound (14) is preferably trialkyl orthooctanoate [$C_7H_{15}C(OR^7)_3$], and more preferably trimethyl orthooctanoate.

The acid used is not limited so long as it promotes acylation reaction of a hydroxyl group in which an ortho ester is used, and may be for example, an organic acid such as acetic acid, propionic acid, trifluoroacetic acid and pentafluoropropionic acid, an organic sulfonic acid such as p-toluenesulfonic acid, camphorsulfonic acid and trifluoromethanesulfonic acid, or an inorganic acid such as hydrogen chloride, hydrogen bromide, hydrogen iodide, phosphoric acid, sulfuric acid and nitric acid, preferably an organic sulfonic acid or an inorganic acid, more preferably p-toluenesulfonic acid, sulfuric acid or hydrogen chloride, and most preferably hydrogen chloride.

The solvent used is preferably an alcohol, and most preferably methanol. The solvent used is preferably an alcohol represented by the formula $R^7OH$ [wherein $R^7$ is the same as $R^7$ of compound (14)].

The reaction temperature is preferably −30° C. to 80° C., and more preferably 0° C. to 50° C.

The reaction time is preferably 5 minutes to 20 hours, and more preferably 10 minutes to 5 hours.

In Step A-10, compound (I) [which may contain a compound represented by the formula (II)] may be produced also by reacting compound (13) with compound (15) and a compound represented by the formula $R^7$—OH in the presence of acid. Compound (15) can be produced in accordance with Process G.

In this step, compound (15) is preferably a compound represented by the formula (15a):

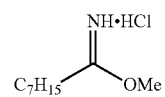

(15a)

The acid used is not limited so long as it promotes the present reaction, and is preferably the aforementioned organic sulfonic acid or inorganic acid, more preferably p-toluenesulfonic acid, sulfuric acid, or hydrogen chloride, and most preferably hydrogen chloride.

The solvent used is preferably an alcohol, and most preferably methanol. The solvent used is preferably an alcohol represented by the formula $R^7OH$ [wherein $R^7$ is the same as $R^7$ of compound (15)].

The reaction temperature is preferably −30° C. to 80° C., and more preferably 0° C. to 50° C.

The reaction time is preferably 5 minutes to 20 hours, and more preferably 10 minutes to 5 hours.

(Process B)

The production of compound (12) from compound (9) in Process A can also be conducted in accordance with Process B.

(Step B-1)

Step B-1 is a procedure to reduce compound (9) by using triphenylphosphine and water, to produce compound (16).

The solvent used is preferably an ether or an ester, more preferably tetrahydrofuran or ethyl acetate, and most preferably ethyl acetate.

The reaction temperature is preferably 20° C. to 120° C., and more preferably 50° C. to 90° C.

The reaction time is preferably 10 minutes to 20 hours, and more preferably 30 minutes to 5 hours.

(Step B-2)

Step B-2 is a procedure to allow compound (16) to react with compound (11) to produce compound (17).

The solvent used is preferably an ether or an ester, more preferably tetrahydrofuran or ethyl acetate, and most preferably ethyl acetate.

The reaction temperature is preferably −30° C. to 80° C., and more preferably 0° C. to 50° C.

The reaction time is preferably 1 to 80 hours, and more preferably 5 to 40 hours.

(Step B-3)

Step B-3 is a procedure to treat compound (17) with a base to produce compound (12).

The base used is not limited so long as it promotes elimination of a cyclic carbonate group and hydrolysis of an ester group, and may be for example, an alkali metal carbonate, an alkali metal hydrogencarbonate, an alkali metal hydroxide, or an alkaline earth metal hydroxide as indicated in Step A-7b, preferably an alkali metal carbonate or an alkali metal hydroxide, more preferably sodium carbonate or potassium carbonate, and most preferably potassium carbonate.

The solvent used is preferably an alcohol, and more preferably methanol. In the present step, it is preferable that water is present.

The reaction temperature is preferably −30° C. to 80° C., and more preferably 0° C. to 50° C.

The reaction time is preferably 30 minutes to 20 hours, and more preferably 1 to 10 hours.

In the case where the protective group of 1,2-diol is a cyclic acetal or a cyclic ketal, deprotection of the protective group of 1,2-diol is conducted by treating compound (17) with a base and then adjusting the pH of the reaction mixture to acidic.

(Process C)

The production of compound (12) from compound (8) in Process A can also be conducted in accordance with Process C.

(Step C-1)

Step C-1 is a procedure to allow compound (8) to react with a compound represented by the formula NaOR$^3$ to produce compound (18).

In Step C-1, the compound represented by the formula NaOR$^3$ is preferably sodium methoxide.

Step C-1 can be conducted in a similar manner to Step A-3.

(Step C-2)

Step C-2 is a procedure to allow compound (18) to react with acetic acid anhydride in the presence of acid or base, to produce compound (19).

In Step C-2, in the case where an acid is used, it can be conducted in a similar manner to Step A-2.

In Step C-2, in the case where a base is used, the base used is preferably an organic base as indicated in Step A-4, more preferably triethylamine, tributylamine, N,N-diisopropylethylamine, 4-dimethylaminopyridine, or a mixture thereof, and most preferably a mixture of triethylamine and 4-dimethylaminopyridine.

The solvent used is preferably an aromatic hydrocarbon, an ester, or a mixture thereof, more preferably an ester, and most preferably ethyl acetate.

The reaction temperature is preferably −30° C. to 80° C., and more preferably 0° C. to 50° C.

The reaction time is preferably 5 minutes to 10 hours, and more preferably 10 minutes to 5 hours.

(Step C-3)

Step C-3 is a procedure to allow compound (19) to react with trimethylsilyl azide in the presence of a Lewis acid, to produce compound (20).

Step C-3 can be conducted in a similar manner to Step A-6.

(Step C-4)

Step C-4 is a procedure to reduce compound (20) by using triphenylphosphine and water, to produce compound (21).

Step C-4 can be conducted in a similar manner to Step B-1.

(Step C-5)

Step C-5 is a procedure to allow compound (21) to react with compound (11) to produce compound (22).

Step C-5 can be conducted in a similar manner to Step B-2.

(Step C-6)

Step C-6 is a procedure to treat compound (22) with a base to produce compound (12).

Step C-6 can be conducted in a similar manner to Step B-3.

(Process D)

The production of compound (13) from compound (9) in Process A can also be conducted in accordance with Process D.

(Step D-1)

Step D-1 is a procedure to reduce compound (9) by using triphenylphosphine and water to produce compound (16).

Step D-1 can be conducted in a similar manner to Step B-1.

(Step D-2)

Step D-2 is a procedure to allow compound (16) to react with compound (23a) to produce compound (24).

In this procedure, a base (preferably an organic amine or an alkali metal hydroxide, more preferably an alkali metal hydroxide) may be further used for the purpose of controlling the pH during the reaction.

The solvent used is preferably an alcohol, water, or a mixture thereof, and most preferably a mixture of methanol and water.

The reaction temperature is preferably −20° C. to 70° C., and more preferably 0° C. to 50° C.

The reaction time is preferably 1 to 200 hours, and more preferably 10 to 100 hours.

The pH during the reaction is preferably 7 to 10, and more preferably 7 to 9.

(Step D-3)

Step D-3 is a procedure to treat compound (24) with a base to produce compound (13).

Step D-3 can be conducted in a similar manner to Step B-3.

(Process E)

The production of compound (13) from compound (10) in Process A can also be conducted in accordance with Process E.

(Step E-1)

Step E-1 is a procedure to allow compound (10) to react with compound (23a) to produce compound (13).

Step E-1 can be conducted in a similar manner to Step D-2.

(Process F)

Process F shows a method of manufacturing compound (11).

(Step F-1)

Step F-1 is a procedure to allow compound (23a) to react with di-t-butyl dicarbonate (Boc$_2$O) in the presence of a base to produce compound (25). Compound (23a) is either publicly known, or can easily be produced from a publicly known compound.

The base used is not limited so long as it is used for protection of an amino group by a tert-butoxycarbonyl group, and may be for example, an alkali metal carbonate, an alkali metal hydrogencarbonate, an alkali metal hydroxide, an alkaline earth metal hydroxide, an alkali metal hydride, or an organic amine as indicated in Step A-4, preferably an organic amine, and most preferably N,N-diisopropylethylamine.

The solvent used is preferably an amide, and most preferably N,N-dimethylformamide.

The reaction temperature is preferably −30° C. to 80° C., and more preferably 0° C. to 50° C.

The reaction time is preferably 30 minutes to 20 hours, and more preferably 1 to 5 hours.

(Step F-2)

Step F-2 is a procedure to allow compound (25) to react with a base to generate an anion of compound (25), and then allow it to react with di-t-butyl dicarbonate to produce compound (11).

The base used is not limited so long as it is used for protection of an imino group by a tert-butoxycarbonyl group, and may be for example, an alkali metal carbonate, an alkali metal hydrogencarbonate, an alkali metal hydroxide, an alkaline earth metal hydroxide, an alkali metal hydride, an alkali metal amide, an alkali metal alkoxide, a lithium alkyl amide, a lithium silyl amide, or an organic amine as indicated in Step A-4, preferably an alkali metal hydride, and most preferably sodium hydride.

The solvent used is preferably an ether, and most preferably tetrahydrofuran.

The reaction temperature of the reaction of compound (25) with the base is preferably −40° C. to 10° C., and more preferably −20° C. to 5° C.

The reaction time of the reaction of compound (25) with the base is preferably 10 minutes to 5 hours, and more preferably 30 minutes to 2 hours.

The reaction temperature of the reaction of the anion with di-tert-butyl dicarbonate is preferably 20° C. to 120° C., and more preferably 50° C. to 90° C.

The reaction time of the reaction of the anion with di-tert-butyl dicarbonate is preferably 30 minutes to 10 hours, and more preferably 1 to 5 hours.

(Process G)

Process G shows a method of manufacturing compound (14) and compound (15).

(Step G-1)

Step G-1 is a procedure to allow compound (26) to react with a compound represented by the formula $R^7OH$ in the presence of an acid represented by the formula HX, to produce compound (15). Compound (26) is either publicly known, or can easily be produced from a publicly known compound.

In Step G-1, the acid represented by the formula HX is preferably hydrogen chloride. In Step G-1, the compound represented by the formula $R^7OH$ is preferably methanol.

The solvent used is preferably an ester, an aliphatic hydrocarbon, or an aromatic hydrocarbon, more preferably an ester, and most preferably methyl acetate.

The reaction temperature is preferably −50° C. to 50° C., and more preferably −20° C. to 20° C.

The reaction time is preferably 1 to 100 hours, and more preferably 5 to 50 hours.

(Step G-2)

Step G-2 is a procedure to allow compound (15) to react with a compound represented by the formula $R^7OH$ to produce compound (14).

In Step G-2, the compound represented by the formula $R^7OH$ is preferably methanol. $R^7$ in the compound represented by the formula $R^7OH$ is preferably the same as $R^7$ of compound (15). The volume ratio of the compound represented by the formula $R^7OH$ with respect to compound (15) is preferably 0.5 to 5, and more preferably 1 to 3.

The solvent used is preferably a solvent which forms a bilayer system. Here, formation of a bilayer system means that the compound represented by the formula $R^7OH$ in the reaction solution and the solvent form two layers that are not uniform and are separate from each other, and by stirring the reaction solution adequately, the compound present in the reaction solution, depending on its lipid solubility or water solubility, can move to the other layer in which the compound can be dissolved more easily. The solvent used is preferably a carbohydrate, more preferably an aliphatic carbohydrate or an aromatic carbohydrate, even more preferably an aliphatic carbohydrate, further preferably cyclohexane, methylcyclohexane or ethylcyclohexane, particularly preferably cyclohexane or methylcyclohexane, and most preferably methylcyclohexane. The compound represented by the formula $R^7OH$ in excess amount can also be used as the solvent.

The mixing ratio (volume ratio) of methylcyclohexane and methanol is preferably 10:1 to 1:2, and more preferably 5:1 to 1:1.

The reaction temperature is preferably −20° C. to 90° C., and more preferably 10° C. to 60° C.

The reaction time is preferably 30 minutes to 30 hours, and more preferably 2 to 15 hours.

The neuraminic acid derivative (I) according to the present invention is known to have excellent neuraminidase inhibitory activity and is therefore useful as a drug for treatment or prevention of influenza (refer to the aforementioned Patent Document 1 or 2).

In the case where the neuraminic acid derivative (I) according to the present invention is used as a medicament, especially as a drug for treatment or prevention of influenza, it can be administered as such, or it can be mixed with a suitable excipient, diluent and the like that are pharmacologically acceptable, and administered as a tablet, capsule, granules, powders, syrup, injection, ointment, liquid formulation, suspension, aerosol, lozenge and the like. The medicament according to the present invention can be administered orally or parenterally, and it is preferable that the compound (I), which is an active ingredient, is administered in such manner that it can be directly delivered to the lungs or respiratory tract (which includes intraoral and intranasal portions).

These pharmaceutical drugs are produced through known methods by using additives such as excipients, binders, disintegrants, lubricants, stabilizers, corrigents for taste or smell, suspending agents, diluents and solvents for formulation.

Although the dosage amount varies depending on symptoms, weight, age and the like of the subject to be administered (a warm-blooded animal, preferably a human), it is preferable to administer it with a lower limit of 0.1 mg (preferably 1 mg) and an upper limit of 1000 mg (preferably 500 mg) per day, once a day or several times a day, depending on symptoms.

EXAMPLES

The present invention will be described in more detail with reference to the following Examples; however, the scope of the present invention is not limited to these.

Example 1

Synthesis of (4S,5R,6R)-5-acetamide-4-guanidino-6-[(1R,2R)-2-hydroxy-1-methoxy-2-(octanoyloxy) propyl]-5,6-dihydro-4H-pyran-2-carboxylic acid [compound (Ib)]

Step A-1: Methyl N-acetylneuramate

Trimethyl orthoformate (116.67 g) and methanol (2720 ml) were added to N-acetyl neuraminic acid (340.00 g) and suspended. Concentrated sulfuric acid (8.63 g) was added to the suspension under stirring at room temperature, and the mixture was stirred for 3 hours at 40° C. The solvent was distilled off under reduced pressure until the amount of solution became approximately 1530 ml, dibutyl ether (4420 ml) was added to the reaction solution at 30° C., and the reaction solution was stirred at the same temperature for 1 hour. After it was further stirred for 1 hour at 0° C., crystals were filtered. The crystals were washed with a mixture of methanol (170 ml) and dibutyl ether (510 ml) and dried under reduced pressure to give the title compound as a white solid (342.11 g, 96.3% yield).

MS (FAB): m/z 324 [M+H]$^+$
HRMS (ESI): Exact mass calcd for $C_{12}H_{22}NO_9$ [M+H]$^+$ 324.12946, Found 324.12966
IR (KBr): 3340, 2938, 1741, 1638, 1553, 1438, 1375, 1279, 1127, 1033 cm$^{-1}$
$^1$H NMR (D$_2$O, 500 MHz): 1.80 (1H, dd, J=12.1, 12.9 Hz), 194 (3H, s), 2.20 (1H, dd, J=5.0, 12.9 Hz), 3.44 (1H, dd, J=1.0, 9.2 Hz), 3.51 (1H, dd, J=6.2, 11.8 Hz), 3.62 (1H, ddd, J=2.8, 6.2, 9.2 Hz), 3.73 (1H, dd, J=2.8, 11.8 Hz), 3.73 (3H, s), 3.81 (1H, dd, J=10.2, 10.2 Hz), 3.95 (1H, ddd, J=5.0, 10.2, 12.1 Hz), 3.96 (1H, dd, J=1.0, 10.2 Hz). $^{13}$C NMR (D$_2$O, 125 MHz): 22.2, 38.7, 52.1, 53.6, 63.2, 66.7, 68.3, 70.2, 70.4, 95.4, 171.5, 174.9.

Step A-2: Methyl (3aS,4R,7aR)-4-[(1S,2R)-1,2,3-triacetoxypropyl]-2-methyl-3a,7a-dihydro-4H-pyrano[3,4-d][1,3]oxazole-6-carboxylate Heptane (600 ml) and anhydrous acetic acid (814.70 g) were added to the compound obtained in Step A-1 (300.00 g) and suspended. The suspension was cooled to 0° C., and concentrated sulfuric acid (209.32 g) was added dropwise under stirring at 40° C. or lower. After stirring the mixture for 4 hours at 40° C., it was cooled to 0° C. and triethylamine (431.93 g) was added dropwise at 40° C. or lower. The reaction solution was added dropwise to a mixture of water (1800 ml), 26% aqueous ammonia (916.79 g) and toluene (4500 ml) which was cooled to 0° C. under stirring at 40° C. or lower. The reaction solution was stirred for 1 hour at 25° C. After the reaction solution was allowed to stand, the organic layer was separated and the solvent was distilled off under reduced pressure until the amount of solution became approximately 900 ml to give a toluene solution of the title compound.

Step A-3: Methyl (3aS,4R,7aR)-4-[(1R,2R)-1,2,3-trihydroxypropyl]-2-methyl-3a,7a-dihydro-4H-pyrano[3,4-d][1,3]oxazole-6-carboxylate Methanol (1800 ml) and 25.4% methanol solution of sodium methoxide (15.79 g) were added to the toluene solution of the compound obtained in Step A-2 at room temperature, and the reaction solution was stirred for 15 minutes at 25° C. The solvent of the reaction solution was distilled off until the amount of solution became approximately 900 ml to give a methanol solution of the title compound.

Step A-4: Methyl (3aS,4R,7aR)-4-{(S)-hydroxy[(4R)-2-oxo-1,3-dioxolan-4-yl]methyl}-2-methyl-3a,7a-dihydro-4H-pyrano[3,4-d][1,3]oxazole-6-carboxylate Dimethyl carbonate (961.26 g) was added to the methanol solution of the compound obtained in Step A-3, and the mixture was stirred for 1 hour at 25° C. and then further for 5 hours at 55° C. The reaction solution was cooled to 0° C., stirred for 5 minutes at the same temperature, and crystals were filtered. The crystals were washed with methanol (600 ml) and dried under reduced pressure to give the title compound as a white solid (234.32 g, 80.6% yield).

MS (FAB): m/z 314 [M+H]$^+$
Anal. calcd for $C_{13}H_{15}NO_8$: C, 49.84; H, 4.83; N, 4.47. Found C, 49.82; H, 4.58; N, 4.46.
IR (KBr): 3194, 1801, 1787, 1734, 1662, 1398, 1277, 1225, 1177, 1089, 988 cm$^{-1}$ $^1$H NMR (DMSO-d6, 500 MHz): 1.89 (3H, s), 3.24 (1H, dd, J=2.0, 10.2 Hz), 3.72 (3H, s), 4.07 (1H, dd, J=2.0, 2.9 Hz), 4.15 (1H, dd, J=8.4, 10.2 Hz), 4.52 (1H, dd, J=7.2, 12.8 Hz), 4.54 (1H, dd, J=8.2, 12.8 Hz), 4.90 (1H, dd, J=4.2, 8.4 Hz), 4.98 (1H, ddd, J=2.9, 7.2, 8.2 Hz), 6.15 (1H, s), 6.27 (1H, d, J=4.2 Hz).
$^{13}$C NMR (DMSO-d6, 125 MHz): 14.3, 53.0, 61.0, 65.9, 67.5, 72.3, 78.3, 78.8, 108.1, 146.8, 155.3, 162.2, 166.3.

Step A-5: Methyl (3aS,4R,7aR)-4-{(S)-methoxy[(4R)-2-oxo-1,3-dioxolan-4-yl]methyl}-2-methyl-3a,7a-dihydro-4H-pyrano[3,4-d][1,3]oxazole-6-carboxylate Tetrahydrofuran (80 ml) and N,N-dimethylacetamide (20 ml) were added to the compound obtained in Step A-4 (20.00 g) and suspended. The suspension was stirred for 15 minutes at 0° C. After 60% sodium hydride (3.32 g) was added to the suspension and the mixture was stirred for 10 minutes at 0° C., dimethyl sulfate (11.27 g) was added, followed by stirring for 2.25 hours at 15° C. Acetic acid (3.83 g) and toluene (200 ml) were added to the reaction solution, the mixture was washed with 5% aqueous sodium hydrogencarbonate (100 ml), and the organic layer 1 and aqueous layer 1 were separated. The organic layer 1 was washed with water (10 ml), and the organic layer 2 and aqueous layer 2 were separated. The aqueous layer 1 and aqueous layer 2 were combined, extracted with toluene (200 ml), and the organic layer 3 was separated. The organic layer 2 and organic layer 3 were combined and the solvent was distilled off under reduced pressure until the amount of solution became approximately 60 ml to give a toluene solution of the title compound.

Step A-6: Methyl (4S,5R,6R)-5-acetamide-4-azide-6-{(S)-methoxy[(4R)-2-oxo-1,3-dioxolan-4-yl]methyl}-5,6-dihydro-4H-pyran-2-carboxylate 2-Methyl-2-propanol (20 ml) and trimethylsilyl azide (14.71 g) were added to the compound obtained in Step A-5 at room temperature. Subsequently, titanium (IV) isopropoxide (5.44 g) was added at 10° C., and the mixture was stirred for 20 hours at 20° C. (stereoisomer ratio 15:1). After the reaction solution was cooled to 0° C., it was stirred for 1 hour at the same temperature, and then crystals were filtered. After the crystals were washed with toluene (40 ml) and dried under reduced pressure to give the title compound as a pale yellowish white solid (20.73 g, 87.7% yield, stereoisomer ratio 66:1)

MS (FAB): m/z 371 [M+H]$^+$

HRMS (ESI): Exact mass calcd for $C_{14}H_{19}N_4O_8$ [M+H$^+$] 371.12029, Found 371.12018

IR (KBr): 3314, 2106, 1795, 1731, 1668, 1550, 1379, 1285, 1180, 1075 cm$^{-1}$ $^1$H NMR (DMSO-d6, 500 MHz): 1.89 (3H, s), 3.36 (3H, s), 3.71 (3H, s), 3.88 (1H, dd, J=1.3, 2.0 Hz), 3.99 (1H, ddd, J=8.9, 9.2, 10.6 Hz), 4.20 (1H, dd, J=1.3, 10.6 Hz), 4.29 (1H, dd, d=2.5, 9.2 Hz), 4.54 (1H, dd, J=7.9, 12.2 Hz), 4.56 (1H, dd, J=7.9, 12.2 Hz), 5.06 (1H, ddd, J=2.0, 7.9, 7.9 Hz), 5.81 (1H, d, J=2.5 Hz), 8.16 (1H, d, J=8.9 Hz). $^{13}$C NMR (DMSO-d6, 125 MHz): 23.4, 47.0, 53.0, 59.0, 61.7, 66.1, 76.7, 77.7, 79.1, 108.6, 144.7, 155.0, 161.7, 170.1.

The peak area ratios of the title compound and stereoisomer thereof were measured under the following HPLC measurement conditions.

HPLC measurement conditions (3)

Column: L-column ODS (4.6 mmID×250 mm, particle diameter 5 μm, manufactured by Chemicals Evaluation and Research Institute)

Column temperature: 40° C.

Measurement wavelength: 254 nm

Mobile phase: acetonitrile: 0.02 mol/l aqueous ammonium acetate solution=65:35

Flow rate: 1 ml/min

Retention time of the title compound: approximately 6.3 minutes

Retention time of stereoisomer: approximately 6.6 minutes.

Step A-7: (4S,5R,6R)-5-Acetamide-4-amino-6-[(1R,2R)-2,3-dihydroxy-1-methoxypropyl]-5,6-dihydro-4H-pyran-2-carboxylic acid Triphenylphosphine (3.90 g) and tetrahydrofuran (20 ml) were added to the compound obtained in Step A-6 (5.00 g) at room temperature, and the mixture was stirred for 10 minutes at 50° C. To the reaction solution were added water (12.5 ml) and 25% aqueous sodium hydroxide (6.48 g) at 50° C., followed by stirring for 2 hours at the same temperature. The reaction solution was cooled to 0° C., concentrated hydrochloric aid (2.74 g) was added and the mixture was allowed to stand. Subsequently, the aqueous layer was separated to give an aqueous solution of the title compound.

Step A-8: (4S,5R,6R)-5-Acetamide-4-[2,3-bis(tert-butoxycarbonyl)guanidino]-6-[(1R,2R)-2,3-dihydroxy-1-methoxypropyl]-5,6-dihydro-4H-pyran-2-carboxylic acid tert-Butyl(tert-butoxycarbonyliminopyrazol-1-yl-methyl)carbamate (4.19 g) and methanol (40 ml) were added to the aqueous solution of the compound obtained in Step A-7 at room temperature, and the mixture was stirred for 43 hours at the same temperature. To the reaction solution was added water (12.5 ml) and the pH was adjusted to 8.35 by concentrated hydrochloric acid. Subsequently, the solvent was distilled off under reduced pressure until the amount of solution became approximately 25 ml. The obtained solution was washed with ethyl acetate (25 ml) 3 times, and the aqueous layer was separated. After the pH of the aqueous layer was adjusted to 2.75 with concentrated hydrochloric acid, it was extracted with ethyl acetate (45 ml) twice. The organic layers were combined, and the solvent was distilled off under reduced pressure until the amount of solution became approximately 20 ml. Water (20 ml) was added to the concentrated solution, and the solvent was distilled off until the amount of solution became approximately 20 ml to give an aqueous solution of the title compound.

Step A-9: (4S,5R,6R)-5-Acetamide-4-guadino-6-[(1R,2R)-2,3-dihydroxy-1-methoxypropyl]-5,6-dihydro-4H-pyran-2-carboxylic acid The aqueous solution of the compound obtained in Step A-8 was stirred for 3.7 hours at 80° C. After the reaction solution was cooled to 0° C., methanol (50 ml) was added thereto, the mixture was stirred for 1.25 hours at the same temperature, and crystals were filtered. The crystals were washed with methanol (10 ml) and dried under reduced pressure to give the title compound as a white solid (3.34 g, 71.4% yield).

MS (FAB): m/z 347[M+H]$^+$

Anal. calcd for $C_{13}H_{22}N_4O_7$: C, 45.08; H, 6.40; N, 16.18. Found C, 44.85; H, 6.16; N, 16.09.

IR (KBr): 3440, 3375, 3256, 1699, 1653, 1587, 1401, 1329, 1284, 1171, 1087, 1029 cm$^{-1}$ $^1$H NMR (D$_2$O, 500 MHz): 1.94 (3H, s), 3.31 (3H, s), 3.45 (1H, dd, J=1.5, 8.6 Hz), 3.57 (1H, dd, J=5.6, 12.0 Hz), 3.78 (1H, dd, J=3.0, 12.0 Hz), 3.88 (1H, ddd, J=3.0, 5.6, 8.6 Hz), 4.10 (1H, dd, J=9.7, 9.7 Hz), 4.30 (1H, dd, J=1.5, 9.7 Hz), 4.30 (1H, dd, J=2.2, 9.7 Hz), 5.52 (1H, d, J=2.2 Hz).

$^{13}$C NMR (D$_2$O, 125 MHz): 22.1, 47.7, 51.8, 60.5, 62.5, 69.6, 75.7, 77.8, 104.0, 149.4, 157.0, 169.0, 174.2.

Step A-10: (4S,5R,6R)-5-Acetamide-4-guadino-6-[(1R,2R)-2-hydroxy-1-methoxy-2-(octanoyloxy)propyl]-5,6-dihydro-4H-pyran-2-carboxylic acid [compound (Ib)]

Methanol (15 ml) and trimethyl orthooctanoate (5.31 g) were added to the compound obtained in Step A-9 (3.00 g) and suspended. To the suspension was added a 1 mol/l hydrogen chloride methanol solution (9.3 ml) at room temperature, followed by stirring for 1 hour at the same temperature. The solvent was distilled off under reduced pressure until the amount of solution became approximately 10.5 ml, and water (30 ml) was added to the reaction solution and the mixture was washed with ethyl acetate (15 ml) twice. The aqueous layer was separated, and pH was adjusted to 7 with a 16.5% aqueous sodium carbonate solution. After stirring the reaction solution for 10 minutes at room temperature, pH was adjusted to 8.8 with a 16.5% aqueous sodium carbonate solution, and then the reaction solution was stirred for 2 hours while maintaining the same pH. Subsequently, pH was adjusted to 5.7 with concentrated hydrochloric acid at room temperature, and the reaction solution was stirred for 1 hour at 0° C. while maintaining the same pH. Crystals were filtered, washed with water (12 ml), and dried under reduced pressure. The crystals were allowed to absorb moisture at room temperature in the atmosphere for 5 hours to give the crude title compound as white crystals (3.89 g, 95.1% yield). Methanol (12 ml) was added to the crude title compound (2.00 g) to dissolve it at 37° C. After methanol (2 ml) and water (28 ml) were added to the solution at the same temperature, the solution was stirred for 1 hour at 25° C., and then crystals were filtered. The crystals were washed with a mixture of methanol (2 ml) and water (4 ml), followed by drying under reduced pressure. The crystals were allowed to absorb moisture at room temperature in the atmosphere for 5 hours to give the title compound as a white crystal (1.84 g, 92.0% yield, chemical purity: 99.72%, compound (Ib):compound (IIb)=97:3, content of compound (13) [R$^2$=methyl group]: 0.02%, content of compound (VII) [$R^1$=1-heptyl group, $R^2$=methyl group]: 0.08%, content of compound (VIII) [$R^1$=1-heptyl group]: 0.04%).

MS (FAB): m/z 473[M+H]$^+$

KF moisture value: 3.9%

Anal. calcd for $C_{21}H_{36}N_4O_8 \cdot 1.065H_2O$: C, 51.29; H, 7.82; N, 11.39.

Found C, 51.21; H, 7.82; N, 11.32.

IR (KBr): 3334, 3289, 2929, 1736, 1665, 1640, 1401, 1325, 1283, 1173, 1114 cm$_{-1}$ $^1$H NMR (CD$_3$OD, 500 MHz): 0.88 (3H, t, J=7.0 Hz), 1.25-1.34 (8H, m), 1.62 (2H, tt, J=7.2, 7.5 Hz), 1.99 (3H, s), 2.35 (2H, t, J=7.5 Hz), 3.38 (3H, s), 3.45 (1H, dd, J=2.5, 8.2 Hz), 4.09-4.14 (2H, m), 4.23 (1H, dd, J=9.0, 9.0 Hz), 4.29-4.36 (3H, m), 5.55 (1H, d, J=2.5 Hz).

$^{13}$C NMR (CD$_3$OD, 125 MHz): 13.1, 21.5, 22.3, 24.7, 28.8, 28.9, 31.5, 33.7, 47.8, 51.4, 60.0, 65.5, 67.4, 76.1, 78.9, 102.3, 150.3, 157.6, 168.1, 172.2, 174.1.

Example 2

Synthesis of methyl (3aS,4R,7aR)-4-{(S)-hydroxy[(4R)-2-oxo-1,3-dioxolan-4-yl]methyl}-2-methyl-3a,7a-dihydro-4H-pyrano[3,4-d][1,3]oxazole-6-carboxylate (compound (7) [$R^4$,$R^5$=oxo group])

Step A-1: Methyl N-acetylneuramate

Trimethyl orthoformate (5.14 g) and methanol (120 ml) were added to N-acetyl neuraminic acid (1) (15.00 g) and suspended. Concentrated sulfuric acid (0.38 g) was added at room temperature under stirring, and the reaction solution was stirred for 3 hours at 40° C. After the completion of the reaction, N,N-dimethylacetamide (15 ml) was added to the reaction solution, and then the solvent was distilled off under reduced pressure until the amount of solution became approximately 40 ml. Water (7.5 ml) and ethyl acetate (150 ml) were added to the concentrated solution at 20° C., the mixture was stirred for 0.5 hours at 30° C., and then ethyl acetate (150 ml) was added and stirred for another 0.5 hours at the same temperature. After stirring for 2 hours at 0° C., crystals were filtered, and the crystals were washed with ethyl acetate (30 ml) which was cooled to 0° C. to give moist crystals of the title compound (15.65 g).

Step A-2: Methyl (3aS,4R,7aR)-4-[(1S,2R)-1,2,3-triacetoxypropyl]-2-methyl-3a,7a-dihydro-4H-pyrano[3,4-d][1,3]oxazole-6-carboxylate Anhydrous acetic acid (25.72 g) was added to the moist crystals obtained in Step A-1 (10.08 g) and suspended, and then concentrated sulfuric acid (6.61 g) was slowly added dropwise under stirring while maintaining the temperature at 40° C. or lower. After stirring the reaction solution for 5 hours at 40° C., the reaction solution was cooled to 0° C., and triethylamine (13.64 g) was added dropwise at 40° C. or lower. This reaction solution was added dropwise to a cooled solution mixture of water (50 ml), 28% aqueous ammonia (27.27 g), and toluene (140 ml) while maintaining the temperature at 40° C. or lower. The reaction solution was further stirred for 1 hour at 25° C. After the reaction solution was allowed to stand, the separated organic layer was washed twice with water (20 ml). The solvent was distilled off under reduced pressure until the amount of solution became approximately 30 ml to give a toluene solution of the title compound.

Step A-3: Methyl (3aS,4R,7aR)-4-[(1R,2R)-1,2,3-trihydroxypropyl]-2-methyl-3a,7a-dihydro-4H-pyrano[3,4-d][1,3]oxazole-6-carboxylate Methanol (60 ml) and a 28% sodium methoxide methanol solution (0.45 g) were added to the toluene solution of the compound obtained in Step A-2 at room temperature, and the mixture was stirred for 15 minutes at 25° C. Subsequently, the reaction solution was concentrated under reduced pressure until the amount of solution became approximately 30 ml to give a methanol solution of methyl (3aS,4R,7aR)-4-[(1R,2R)-1,2,3-trihydroxypropyl]-2-methyl-3a,7a-dihydro-4H-pyrano[3,4-d][1,3]oxazole-6-carboxylate (4).

Step A-4: Methyl (3aS,4R,7aR)-4-{(S)-hydroxy[(4R)-2-oxo-1,3-dioxolan-4-yl]methyl}-2-methyl-3a,7a-dihydro-4H-pyrano[3,4-d][1,3]oxazole-6-carboxylate Dimethyl carbonate (30.35 g) was added to the methanol solution of the compound obtained in Step A-3. The mixture was stirred for 1 hour at 25° C., and further stirred for 5 hours at 55° C. The reaction solution was cooled to 0° C., stirred for 5 minutes at the same temperature, and then crystals were filtered. The crystals were washed with methanol (20 ml) and dried under reduced pressure to give the title compound as a white solid (7.06 g, 76.9% yield).

Example 3

Synthesis of (4S,5R,6R)-5-acetamide-4-guadino-6-[(1R,2R)-2,3-dihydroxy-1-methoxypropyl]-5,6-dihydro-4H-pyran-2-carboxylic acid (compound (13) [$R^2$=methyl group])

Step B-1: Methyl (4S,5R,6R)-5-acetamide-4-amino-6-{(S)-methoxy[(4R)-2-oxo-1,3-dioxolan-4-yl]methyl}-5,6-dihydro-4H-pyran-2-carboxylate Ethyl acetate (40 ml), triphenylphosphine (7.79 g), and water (1.94 g) were added to the compound (10.00 g) obtained in Step A-6 of Example 1 at room temperature, followed by stirring for 2.5 hours at 72° C. The reaction solution was cooled to room temperature to give an ethyl acetate solution of the title compound.

Step B-2: Methyl (4S,5R,6R)-5-acetamide-4-[2,3-bis(tert-butoxycarbonyl)guanidino]-6-{(S)-methoxy[(4R)-2-oxo-1,3-dioxolan-4-yl]methyl}-5,6-dihydro-4H-pyran-2-carboxylate tert-Butyl(tert-butoxycarbonyliminopyrazol-1-yl-methyl)carbamate (8.80 g) was added to the ethyl acetate solution of the compound obtained in Step B-1 at room temperature, and the mixture was stirred for 17.5 hours at the same temperature. The solvent was distilled off under reduced pressure until the amount of solution became approximately 30 ml, toluene (100 ml) was added, and then insoluble matter was filtered. The filtrate was washed twice with water (30 ml), and the solvent of the separated organic layer was distilled off under reduced pressure until the amount of solution became approximately 40 ml to give a toluene solution of the title compound.

Step B-3: (4S,5R,6R)-5-Acetamide-4-[2,3-bis(tert-butoxycarbonyl)guanidino]-6-[(1R,2R)-2,3-dihydroxy-1-methoxypropyl]-5,6-dihydro-4H-pyran-2-carboxylic acid Methanol (50 ml), water (23 ml), and potassium carbonate (11.20 g) were added to the toluene solution of the compound obtained in Step B-2 at room temperature, and the mixture was stirred for 4 hours at the same temperature. The reaction solution was cooled to 5° C., water (50 ml) was added, and then pH was adjusted to 8.3 by 7% hydrochloric acid. The solvent of the reaction solution was distilled off under reduced pressure until the amount of solution became approximately 110 ml, followed by washing with ethyl acetate (50 ml) 3 times, and the aqueous layer was separated. The pH of the aqueous layer was adjusted to 2.7 with 7% hydrochloric acid, followed by extracting with ethyl acetate (90 ml) twice. The organic layers were combined, and the solvent was distilled off until the amount of solution became approximately 40 ml. Water (40 ml) was added to the concentrated solution, and the solvent was distilled off under reduced pressure until the amount of solution became approximately 40 ml to give an aqueous solution of the title compound.

Step A-9: (4S,5R,6R)-5-Acetamide-4-guadino-6-[(1R,2R)-2,3-dihydroxy-1-methoxypropyl]-5,6-dihydro-4H-pyran-2-carboxylic acid (compound (13) [$R^2$=methyl group])

The aqueous solution of the compound obtained in Step B-3 was subjected to a similar operation to Step A-9 of Example 1 to give the title compound as a white solid (6.71 g, 71.8% yield).

Example 4

Synthesis of (4S,5R,6R)-5-acetamide-4-guadino-6-[(1R,2R)-2,3-dihydroxy-1-methoxypropyl]-5,6-dihydro-4H-pyran-2-carboxylic acid (compound (13) [$R^2$=methyl group])

Step C-1: Methyl (3aS,4R,7aR)-4-[(1R,2R)-2,3-dihydroxy-1-methoxypropyl]-2-methyl-3a,7a-dihydro-4H-pyrano[3,4-d][1,3]oxazole-6-carboxylate Methanol (460 ml) and a 25.4% sodium methoxide methanol solution (14.36 g) were added to a toluene solution (approximately 675 ml) of a compound, which was obtained by subjecting methyl (3aS,4R,7aR)-4-{(S)-hydroxy[(4R)-2-oxo-1,3-dioxolan-4-yl]methyl}-2-methyl-3a,7a-dihydro-4H-pyrano[3,4-d][1,3]oxazole-6-carboxylate (46.00 g) to Step A-5 of Example 1, at room temperature, and the mixture was stirred for 30 minutes at the same temperature. The solvent of the reaction solution was distilled off under reduced pressure until the amount of solution became approximately 138 ml, methanol (460 ml) was added, and the reaction solution was stirred for 30 minutes at room temperature. After acetic acid (4.41 g) was added to the reaction solution and the solvent was distilled off under reduced pressure until the amount of solution became approximately 138 ml, toluene (230 ml) was added to the reaction solution and then the solvent was distilled off again under reduced pressure until the amount of solution became 138 ml to give a toluene suspension of the title compound.

Step C-2: Methyl (3aS,4R,7aR)-4-[(1S,2R)-2,3-diacetoxy-1-methoxypropyl]-2-methyl-3a,7a-dihydro-4H-pyrano[3,4-d][1,3]oxazole-6-carboxylate Ethyl acetate (184 ml) was added to the toluene suspension of the compound obtained in Step C-1 and the mixture was stirred for 30 minutes at room temperature. Subsequently, triethylamine (66.69 g), N,N-dimethylaminopyridine (0.90 g), and anhydrous acetic acid (34.47 g) were added at 20° C. or lower, and the mixture was stirred for 1 hour at room temperature. Toluene (460 ml) and 5% aqueous sodium hydrogencarbonate (230 ml) were added to the reaction solution, followed by stirring for 1 hour at room temperature. After allowing the reaction solution to stand, the organic layer was separated and washed with 5% aqueous sodium hydrogencarbonate (230 ml). The organic layer was separated, the solvent was distilled off under reduced pressure until the amount of solution became approximately 230 ml, and then insoluble matter was filtered. The residue was washed with 138 ml of toluene, the filtrate and the solution used for washing were combined, and the solvent was distilled off under reduced pressure until the amount of solution became approximately 138 ml to give a toluene solution of the title compound.

Step C-3: Methyl (4S,5R,6R)-5-acetamide-4-azide-6-[(1S,2R)-2,3-diacetoxy-1-methoxypropyl]-5,6-dihydro-4H-pyran-2-carboxylate 2-Methyl-2-propanol (47 ml) was added to the toluene solution of the compound obtained in Step C-2. After cooling the mixture, titanium (IV) isopropoxide (8.68 g) and trimethylsilyl azide (23.92 g) were added, followed by stirring for 4 hours at 20° C. An aqueous sodium nitrite solution (sodium nitrite 14.32 g, water 329 ml) and hydrochloric acid (concentrated hydrochloric acid 23.77 g, water 74 ml) were added to the reaction solution at 10° C. or lower, and the reaction solution was stirred for 30 minutes at room temperature. Subsequently, the solvent was distilled off under reduced pressure until the amount of solution became approximately 494 ml. The concentrated solution was extracted with ethyl acetate (471 ml), and organic layer 1 and aqueous layer 1 were separated. Aqueous layer 1 was extracted with ethyl acetate (471 ml), and organic layer 2 was separated. Organic layer 1 was washed twice with 5% aqueous sodium hydrogencarbonate (235 ml), and organic layer 3 was separated. Aqueous layer 2 and aqueous layer 3 were combined, extracted with organic layer 2, and organic layer 4 was separated. Organic layer 3 and organic layer 4 were combined, ethyl acetate (80 ml) was added, and the solvent was distilled off under reduced pressure until the amount of solution became approximately 245 ml to give an ethyl acetate solution of the title compound.

Step C-4: Methyl (4S,5R,6R)-5-acetamide-4-amino-6-[(1S,2R)-2,3-diacetoxy-1-methoxypropyl]-5,6-dihydro-4H-pyran-2-carboxylate Triphenylphosphine (35.23 g) and water (8.80 g) were added to the ethyl acetate solution of the compound obtained in Step C-3 at 0° C., and the mixture was stirred for 2 hours at 72° C. The reaction solution was cooled to room temperature to give an ethyl acetate solution of the title compound.

Step C-5: Methyl (4S,5R,6R)-5-acetamide-4-[2,3-bis(tert-butoxycarbonyl)guanidino]-6-[(1S,2R)-2,3-diacetoxy-1-methoxypropyl]-5,6-dihydro-4H-pyran-2-carboxylate tert-Butyl(tert-butoxycarbonyliminopyrazol-1-yl-methyl)carbamate (39.79 g) was added to the ethyl acetate solution of the compound obtained in Step C-4 at room temperature, the mixture was stirred for 1 hour at the same temperature, and was then allowed to stand for 17 hours. After the solvent was distilled off under reduced pressure until the amount of solution became approximately 141 ml, toluene (471 ml) was added to the reaction solution, followed by washing with water (141 ml) and a 10% aqueous sodium chloride solution (141 ml). The solvent of separated organic layer was distilled off under reduced pressure until the amount of solution became approximately 188 ml to give a toluene solution of the title compound.

Step C-6: (4S,5R,6R)-5-Acetamide-4-[2,3-bis(tert-Butoxycarbonyl)guanidino]-6-[(1R,2R)-2,3-dihydroxy-1-methoxypropyl]-5,6-dihydro-4H-pyran-2-carboxylic acid Methanol (235 ml), water (108 ml), and potassium carbonate (50.63 g) were added to the toluene solution of the compound obtained in Step C-5, and the mixture solution was stirred for 4.5 hours at room temperature. Water (235 ml) was added at 30° C. or lower, and then the pH of the mixture was adjusted to 8.3 with 7% hydrochloric acid. The solvent was distilled off under reduced pressure until the amount of solution became approximately 518 ml, the reaction solution was washed with ethyl acetate (235 ml) 3 times, and the aqueous layer was separated. The pH of the aqueous layer was adjusted to 2.7 with 7% hydrochloric acid, followed by extracting with ethyl acetate (423 ml) twice. The organic layers were combined, the solvent was distilled off under reduce pressure until the amount of solution became approximately 282 ml, and the insoluble matter was filtered. The residue was washed with ethyl acetate (376 ml), the filtrate and the solution used for washing were combined, and then the solvent was distilled off under reduced pressure until the amount of solution became approximately 188 ml, Water (188 ml) was added to the concentrated solution, the solvent was distilled off until the amount of solution became approximately 188 ml to give an aqueous solution of the title compound.

Step A-9: (4S,5R,6R)-5-acetamide-4-guadino-6-[(1R,2R)-2,3-dihydroxy-1-methoxypropyl]-5,6-dihydro-4H-pyran-2-carboxylic acid (compound (13) [$R^2$=methyl group])

The aqueous solution of the compound obtained in Step C-6 was subjected to a similar operation to Step A-9 of Example 1 to give the title compound as a white solid (30.97 g, 62.3% yield).

Example 5

Synthesis of (4S,5R,6R)-5-acetamide-4-guadino-6-[(1R,2R)-2,3-dihydroxy-1-methoxypropyl]-5,6-dihydro-4H-pyran-2-carboxylic acid (compound (13) [$R^2$=methyl group])

Step D-1: Methyl (4S,5R,6R)-5-acetamide-4-amino-6-{(S)-methoxy[(4R)-2-oxo-1,3-dioxolan-4-yl]methyl}-5,6-dihydro-4H-pyran-2-carboxylate Ethyl acetate (4 ml), water (0.194 g), and triphenylphosphine (0.78 g) were added to the compound (1.00 g) obtained in Step A-6 of Example 1, and the mixture was stirred for 2 hours at 70° C. The reaction solution was cooled to room temperature, and then the solvent was distilled off under reduced pressure to give the crude title compound.

Step D-2: Methyl (4S,5R,6R)-5-acetamide-4-guanidino-6-{(S)-methoxy[(4R)-2-oxo-1,3-dioxolan-4-yl]methyl}-5,6-dihydro-4H-pyran-2-carboxylate Water (4 ml), methanol (1 ml), and 1H-pyrazole-1-carboxamidine hydrochloride (0.52 g) were added to the crude compound obtained in Step D-1, and the mixture was stirred for 65 hours at room temperature to give a solution of the title compound.

Step D-3: (4S,5R,6R)-5-acetamide-4-guadino-6-[(1R,2R)-2,3-dihydroxy-1-methoxypropyl]-5,6-dihydro-4H-pyran-2-carboxylic acid (compound (13) [$R^2$=methyl group])

Methanol (1 ml) and potassium carbonate (0.75 g) were added to the compound obtained in Step D-2, and after the mixture was stirred for approximately 23 hours at room temperature, the amount of the title compound generated was measured by HPLC (amount generated 0.59 g, yield 63.3%).
HPLC measurement conditions (4)
Column: L-column ODS (4.6 mmID×250 mm, particle diameter 5 μm, manufactured by Chemicals Evaluation and Research Institute)
Column temperature: 40° C.
Measurement wavelength: 210 nm
Mobile phase: 0.01M potassium dihydrogen phosphate buffer'(pH 3)/methanol/PIC B-7 (Low UV, manufactured by Waters Corporation) (950/50/1)
Flow rate: 1 ml/min
Retention time of the title compound: approximately 4.1 minutes.

Example 6

Synthesis of (4S,5R,6R)-5-acetamide-4-guadino-6-[(1R,2R)-2,3-dihydroxy-1-methoxypropyl]-5,6-dihydro-4H-pyran-2-carboxylic acid (compound (13) [$R^2$=methyl group])

Step E-1: To an aqueous solution of a compound obtained by subjecting methyl (4S,5R,6R)-5-acetamide-4-azide-6-{(S)-methoxy[(4R)-2-oxo-1,3-dioxolan-4-yl]methyl}-5,6-dihydro-4H-pyran-2-carboxylate (1.00 g) to a similar operation to Step A-7, was added 1H-pyrazole-1-carboxamidine hydrochloride (1.01 g) in two portions. The mixture was stirred for approximately 100 hours at room temperature while maintaining the pH in the range of 7 to 9. The amount of the title compound generated was measured under the HPLC measurement conditions (4) (amount generated 0.53 g, yield 56.5%).

Example 7

Synthesis of (4S,5R,6R)-5-acetamide-4-guadino-6-[(1R,2R)-2-hydroxy-1-methoxy-2-(octanoyloxy)propyl]-5,6-dihydro-4H-pyran-2-carboxylic acid [compound (Ib)]

Methanol (20 ml) was added to methyl octaneimidoate hydrochloride (8.39 g), and the mixture was stirred for 3 hours at 35° C. Subsequently, the compound (5.00 g) obtained in Step A-9 of Example 1 and methanol (5 ml) were added at room temperature, and suspended. A 1.6 mol/l hydrogen chloride methanol solution (10.4 ml) was added to this suspension at room temperature, followed by stirring for 2 hours at the same temperature. The solvent was distilled off until the amount of solution became approximately 20 ml, and water (60 ml) was added, followed by washing twice with ethyl acetate (25 ml). The aqueous layer was separated, and the pH was adjusted to 7 with a 20% aqueous sodium carbonate solution, followed by stirring for 5 minutes at room temperature. Subsequently, the pH was adjusted to 8.7 with a 20% aqueous sodium carbonate solution, the reaction solution was stirred for 1.5 hours, and then crystals were filtered. The crystals were washed with water (10 ml), and then dried under reduced pressure to give the crude title compound as white crystal (6.21 g, 91.3% yield, chemical purity: 99.51% compound (Ib):compound (IIb)=95:5, content of compound (13) [$R^2$=methyl group]: <0.01%, content of compound (VII) [$R^1$=1-heptyl group, $R^2$=methyl group]: 0.06%, content of compound (VIII) [$R^1$=1-heptyl group]: 0.09%).

Example 8

Synthesis of tert-butyl(tert-butoxycarbonyliminopyrazol-1-yl-methyl)carbamate [compound (11)]

Step F-1: N,N-dimethylformamide (350 ml) and N,N-diisopropyl ethylamine (125 ml) were added to tert-butyl(iminopyrazol-1-yl-methyl)carbamate 1H-pyrazole-1-carboxamidine hydrochloride (100 g), and then a N,N-dimethylformamide (50 ml) solution of ditert-butyl dicarbonate (152 g) was added over 40 minutes at room temperature. After the mixture was stirred for 2 hours at the same temperature, water (500 ml) was added, the mixture was extracted with toluene (500 ml), and organic layer 1 and aqueous layer 1 were separated. Organic layer 1 was further washed twice with water (300 ml), and organic layer 2 was separated. Aqueous layer 1 was extracted with toluene (500 ml), and organic layer 3 was separated. Organic layer 2 and organic layer 3 were combined, and the solvent was distilled off under reduced pressure until the amount of the solution became approximately 300 ml. Hexane (500 ml) was added to the resulting solution at room temperature, the mixture was stirred for 30 minutes, followed by stirring for 30 minutes under ice-cooling, and then crystals were filtered. The crystals were washed with hexane (100 ml), and then dried under reduced pressure to give the title compound (120.3 g, 83.9% yield).

Step F-2: tert-Butyl(tert-butoxycarbonyliminopyrazol-1-yl-methyl)carbamate [compound (11)]

A tetrahydrofuran (100 ml) solution of the compound (50 g) obtained in Step B-1 was added to a tetrahydrofuran (100 ml) suspension of 60% sodium hydride (9.99 g) over 1 hour while maintaining the temperature in the range of −5° C. to 0° C. After the mixture was stirred for 30 minutes at the same temperature, a tetrahydrofuran (100 ml) solution of ditert-butyl dicarbonate (57.1 g) was added while maintaining the temperature from −5° C. to 0° C., and then tetrahydrofuran (250 ml) was added. After the reaction solution was stirred for 2 hours under reflux, acetic acid (20.4 ml) was added at room temperature, and the solvent was distilled off under reduced pressure until the amount of solution became approximately 150 ml. A 5% aqueous sodium hydrogencarbonate solution (500 ml) was added to the resulting solution and the mixture was extracted with ethyl acetate (500 ml). The organic layer was washed with water (150 ml), and the solvent was distilled off until the amount of solution became approximately 75 ml. Hexane (200 ml) was added to the residue at room temperature, and seed crystal was inoculated. After stirring the solution for 40 minutes under ice-cooling, crystals were filtered, washed with hexane (50 ml), and dried under reduced pressure to give the title compound (54.47 g, 73.8% yield).

$^1$H NMR (CDCl$_3$, 500 MHz): 1.49 (9H, s), 1.55 (9H, s), 6.41 (1H, dd, J=1.5, 2.7 Hz), 7.62 (1H, dd, J=0.7, 1.5 Hz), 8.30 (1H, dd, J=0.7, 2.7 Hz), 8.93 (1H, brs).

$^{13}$C NMR (CDCl$_3$, 125 MHz): 28.1, 28.2, 81.4, 83.4, 109.8, 129.0, 139.2, 142.8, 149.4, 157.4.

Example 9

Synthesis of trimethyl orthooctanoate (compound (14) [$R^1$=1-heptyl group, $R^7$=methyl group])

Step G-1: Methyl octanimidate hydrochloride

Methanol (2.81 g) and methyl acetate (30 ml) were added to octanenitrile (10.00 g), and the mixture was cooled to 0° C. Hydrogen chloride (7.50 g) was added and the mixture was stirred for 25 hours at the same temperature. Methylcyclohexane (60 ml) was added to the reaction solution, and then the solvent was distilled off under reduced pressure. Methylcyclohexane (20 ml) was added to the residue, the mixture was stirred for 1.5 hours at room temperature, and then crystals were filtered. The crystals were washed with methylcyclohexane and dried under reduced pressure to give the title compound as a white solid (14.45 g, 93.4% yield).

MS (FAB): m/z 158 [M+H]$^+$

HRMS (ESI): Exact mass calcd for C$_9$H$_{20}$NO [M+H]$^+$ 158.15449, Found 158.15433

IR (KBr): 3139, 3109, 2925, 2857, 1712, 1627, 1474, 1411, 1213, 1100 cm$^{-1}$ $^1$H NMR (CDCl$_3$, 500 MHz): 0.82 (3H, t, J=7.0 Hz), 1.19-1.33 (8H, m), 1.67 (2H, tt, J=7.5, 7.8 Hz), 2.70 (2H, t, J=7.8 Hz), 4.24 (3H, s), 11.52 (1H, brs), 12.46 (1H, brs).

$^{13}$C NMR (CDCl$_3$, 125 MHz): 14.1, 22.6, 25.7, 28.7, 28.8, 31.5, 32.9, 60.7, 180.5.

Step G-2: Trimethyl orthooctanoate (compound (14) [$R^1$=1-heptyl group, $R^7$=methyl group])

Methylcyclohexane (240 ml) and methanol (80 ml) were added to the compound (40.00 g) obtained in Step G-1, and the mixture was stirred for 6 hours at 35° C. The reaction solution was cooled to 10° C., and methylcyclohexane (20 ml) was added, followed by washing with 5% aqueous sodium hydrogencarbonate (280 ml). The reaction solution was further washed with 5% aqueous sodium hydrogencarbonate (120 ml), and the organic layer was separated. The insoluble matter was filtered, and the residue was washed with methylcyclohexane (20 ml). Then, the filtrate and the solution used for washing were combined, and the solvent was distilled off under reduced pressure. The residue was purified by distillation under reduced pressure (1.5-1.8 torr, b.p. 85-90° C.) to give the title compound as a colorless transparent oil (35.37 g, 83.8% yield).

MS (ESI): m/z 227 [M+Na]$^+$

HRMS (ESI): Exact mass calcd for C$_{11}$H$_{24}$O$_3$Na [M+Na]$^+$ 227.16231, Found 227.16138

IR (neat): 2955, 2928, 2854, 1466, 1241, 1153, 1078, 1047, 977 cm$_{-1}$ $^1$H NMR (CDCl$_3$, 500 MHz): 0.86 (3H, t, J=6.8 Hz), 1.23-1.33 (8H, m), 1.67-1.71 (2H, m), 3.21 (9H, s).

$^{13}$C NMR (CDCl$_3$, 125 MHz): 14.1, 22.7, 22.8, 29.3, 29.5, 30.5, 31.9, 49.4, 116.0.

Comparative Example 1

Synthesis of methyl (4S,5R,6R)-5-acetamide-4-tert-butyldimethylsilyloxy-2-methoxy-6-{(S)-methoxy[(4R)-2,2-dimethyl-1,3-dioxolan-4-yl]methyl}-tetrahydro-4H-pyran-2-carboxylate [compound (VIb)]

60% Sodium hydride (0.16 g) was added to a N,N-dimethylformamide (10 ml) solution of compound (VIa) (1.00 g) described in Process Z at 0° C. The mixture was stirred for 5 minutes at the same temperature and dimethyl sulfate (0.31 g) was added at 0° C., followed by further stirring for 2 hours at room temperature (peak area ratio of the title compound: 41.6%, peak area ratio of N-methylated compound: 12.2%). A saturated aqueous ammonium chloride solution (10 ml) and water (2 ml) were added to the reaction solution, and the mixture was extracted with ethyl acetate (20 ml) 3 times. The organic layer was washed once with 5% aqueous sodium hydrogencarbonate (10 ml) and with water (10 ml) twice. Subsequently, the solvent was distilled off under reduced pressure. Diisopropyl ether (2 ml) was added to the residue, the mixture was stirred for 10 minutes at room temperature, and the mixture was further stirred for 30 minutes at 0° C. After that crystals were filtered. The crystals were washed with diisopropyl ether (2 ml), and dried under reduced pressure to give the title compound as a white solid (0.28 g, 27.3% yield, peak area ratio of the title compound: 97.2%, peak area ratio of N-methylated compound: 0.3%).

The peak area ratios of the title compound and the N-methylated compound were measured in accordance with the following HPLC measurement conditions.
HPLC measurement conditions (4)
Column: L-column ODS (4.6 mmID×250 mm, particle diameter 5 μm, manufactured by Chemicals Evaluation and Research Institute)
Column temperature: 40° C.
Measurement wavelength: 195 nm
Mobile phase: acetonitrile: 0.02 M aqueous potassium dihydrogen phosphate solution=60:40
Flow rate: 1 ml/min
Retention time of the title compound: approximately 8.6 minutes
Retention time of the N-methylated compound: approximately 15.4 minutes

Comparative Example 2

Synthesis of methyl (4S,5R,6R)-5-acetamide-4-azide-6-[(1S,2R)-2,3-diacetoxy-1-methoxypropyl]-5,6-dihydro-4H-pyran-2-carboxylate [compound (IVg)]

N,N-dimethylformamide (250 ml), DOWEX° 50W-X8 (10.0 g), and sodium azide (10.0 g) were added to compound (IVf) (10.0 g) described in Process W, Process Y, and Process Z, and the mixture was stirred for 7 hours at 80° C. (stereoisomer ratio 7:1). The reaction solution was cooled to room temperature, and was filtered through an ion exchange resin. The resin was washed with methanol (50 ml), the solvent used for washing was combined with the filtrate, and the solvent was distilled off under reduced pressure. Dichloromethane (100 ml), saturated aqueous sodium hydrogencarbonate (50 ml), and water (50 ml) were added to the concentrated residue, and the organic layer was separated after stirring. The organic layer was washed with 10% aqueous sodium chloride (100 ml) and the solvent was distilled off under reduced pressure to give the unpurified title compound (10.34 g, stereoisomer ratio 6:1).

The peak area ratios of the title compound and the stereoisomer were measured in accordance with the following HPLC measurement conditions.
HPLC measurement conditions (5)
Column: L-column ODS (4.6 mmID×250 mm, particle diameter 5 μm, manufactured by Chemicals Evaluation and Research Institute)
Column temperature: 40° C.
Measurement wavelength: 254 nm
Mobile phase: acetonitrile: water=60:40
Flow rate: 1 ml/min
Retention time of the title compound: approximately 6.2 minutes
Retention time of stereoisomer: approximately 6.6 minutes

Comparative Example 3

Synthesis of diphenylmethyl (4S,5R,6R)-5-acetamide-4-[2,3-bis(tert-butoxycarbonyl)guanidino]-6-[(1R,2R)-2-hydroxy-1-methoxy-3-(octanoyloxy)propyl]-5,6-dihydro-4H-pyran-2-carboxylate [compound (IVk)]

Dichloromethane (20 ml) and triethylamine (0.10 g) were added to compound (IVj) (0.50 g) of Process W at 0° C., octyl chloride (0.14 g) was added dropwise at the same temperature, and the mixture was stirred for 3.5 hours. Ethyl acetate (50 ml) was added to the reaction solution, and the mixture was washed with saturated aqueous sodium hydrogencarbonate (30 ml) and saturated aqueous sodium chloride (10 ml). The organic layer was separated, dried with anhydrous sodium sulfate, and the solvent was distilled off under reduced pressure to give the unpurified title compound (0.57 g, 97.0% yield, peak area ratio of the title compound: 63.2%, peak area ratio of diacylated compound: 5.6%).

The peak area ratios of the title compound and the diacylated compound were measured in accordance with the following HPLC measurement conditions.
HPLC measurement conditions (6)
Column: L-column ODS (4.6 mmID×250 mm, particle diameter 5 μm, manufactured by Chemicals Evaluation and Research Institute)
Column temperature: 40° C.
Measurement wavelength: 254 nm
Mobile phase: acetonitrile: 0.02 mol/l aqueous ammonium acetate=90:10
Flow rate: 1 ml/min
Retention time of the title compound: approximately 6.8 minutes
Retention time of the diacylated compound: approximately 24.6 minutes

Comparative Example 4

Synthesis of trimethyl orthooctanoate (compound (14) [$R^3$=1-heptyl group, $R^7$=methyl group]

Methanol (330 ml) and petroleum ether (1 L) were added to the compound (160.44 g) obtained in accordance with Step G-1 of Example 9, and the mixture was stirred for 18 hours under reflux. The reaction solution was cooled to 0° C., and was allowed to stand for 2 hours at the same temperature. The insoluble matter was filtered, and the solvent was distilled off under reduced pressure. The residue was purified by distillation under reduced pressure (2.2 torr, b.p. 93-96° C.) to give the title compound as a colorless transparent oil (78.60 g, 44.7% yield).

Comparative Example 5

(4S,5R,6R)-5-Acetamide-4-guadino-6-[(1R,2R)-2-hydroxy-1-methoxy-2-(octanoyloxy)propyl]-5,6-dihydro-4H-pyran-2-carboxylic acid [compound (Ib)]

Compound (Vd) of Process Z was converted into compound (IVj) by the diphenylmethyl esterification reaction of Process W [the third reaction in the conversion procedure of compound (IVi) into compound (IVj)], then converted into compound (Ia) by Process W, and then the title compound was synthesized from compound (Ia) in accordance with the process described in the Example of Patent Document 2. The quality of the synthesized title compound was as follows: Chemical purity: 91.88%, compound (Ib):compound (IIb)= 85:15, content of compound (13) [$R^2$=methyl group]: 3.54%, content of compound (VII) [$R^1$=1-heptyl group, $R^2$=methyl group]: 0.51%, content of compound (VIII) [$R^1$=1-heptyl group]: 0.97%

Preparation Example 1

Liquid Formulation 1

A liquid formulation is prepared containing the compound of Example 1 10% (w/w), benzalkonium chloride 0.04% (w/w), phenethyl alcohol 0.40% (w/w), and purified water 89.56% (w/w).

Preparation Example 2

Liquid formulation 2

A liquid formulation is prepared containing the compound of Example 1 10% (w/w), benzalkonium chloride 0.04% (w/w), polyethylene glycol 400 10% (w/w), propylene glycol 30% (w/w), and purified water 49.96% (w/w).

Preparation Example 3

Powders

A powder formulation is prepared containing the compound of Example 1 40% (w/w) and lactose 60% (w/w).

Preparation Example 4

Aerosol

An aerosol is prepared containing the compound of Example 1 10% (w/w), lecithin 0.5% (w/w), Freon 11 34.5% (w/w) and Freon 12 55% (w/w).

[Industrial Applicability]

The novel method for manufacturing neuraminic acid derivatives via novel synthetic intermediates according to the present invention is superior from an industrial perspective, compared with known manufacturing methods. In addition, neuraminic acid derivatives with high purity can be obtained in high yield by the present manufacturing method.

Since neuraminic acid derivative with high purity, which is obtained by the present production method, has excellent neuraminidase inhibitory activity, it is useful as a drug for prevention or treatment of influenza.

The invention claimed is:

1. A method for manufacturing a compound represented by the following formula (9):

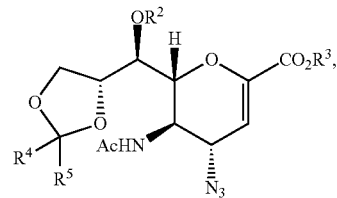

(9)

wherein $R^2$ represents a $C_1$-$C_4$ alkyl group, $R^3$ represents a $C_1$-$C_6$ alkyl group, $R^4$ and $R^5$, independently from each other, represent a hydrogen atom, a $C_1$-$C_6$ alkyl group or a phenyl group, or $R^4$ and $R^5$ together form a tetramethylene group, a pentamethylene group or an oxo group, and Ac represents an acetyl group, comprising:

reacting a compound represented by the following formula (8):

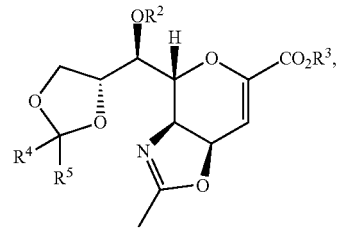

(8)

wherein $R^2$ represents a $C_1$-$C_4$ alkyl group, $R^3$ represents a $C_1$-$C_6$ alkyl group, $R^4$ and $R^5$, independently from each other, represent a hydrogen atom, a $C_1$-$C_6$ alkyl group or a phenyl group, or $R^4$ and $R^5$ together form a tetramethylene group, a pentamethylene group or an oxo group, with trimethylsilyl azide in the presence of a Lewis acid.

2. The manufacturing method according to claim 1, wherein $R^2$ is a methyl group, $R^3$ is a methyl group, $R^4$ and $R^5$ together form an oxo group, and the Lewis acid is titanium (IV) isopropoxide.

* * * * *

UNITED STATES PATENT AND TRADEMARK OFFICE
CERTIFICATE OF CORRECTION

PATENT NO. : 8,575,370 B2
APPLICATION NO. : 13/795050
DATED : November 5, 2013
INVENTOR(S) : Yoshitaka Nakamura et al.

It is certified that error appears in the above-identified patent and that said Letters Patent is hereby corrected as shown below:

On the Title page, References Cited, Column 2, Line 11:

delete "glutumate" and insert --glutamate--.

On page 2 of the Title page, References Cited, Column 1, Line 2:

delete "Oseltamivlr" and insert --Oseltamivir--.

On page 2 of the Title page, References Cited, Column 1, Line 8:

delete "HiNi" and insert --H1N1--.

On page 2 of the Title page, References Cited, Column 1, Line 18:

delete "at" and insert --et--.

On page 2 of the Title page, References Cited, Column 1, Line 19:

delete "Bloorganic" and insert --Bioorganic--.

On page 2 of the Title page, References Cited, Column 1, Line 26:

delete "at" and insert --et--.

On page 2 of the Title page, References Cited, Column 1, Line 26:

delete "Guanidlno" and insert --Guanidino--.

On page 2 of the Title page, References Cited, Column 1, Line 26:

delete "Modifled" and insert --Modified--.

Signed and Sealed this
Twenty-fourth Day of June, 2014

Michelle K. Lee
*Deputy Director of the United States Patent and Trademark Office*

CERTIFICATE OF CORRECTION (continued)
U.S. Pat. No. 8,575,370 B2

On page 2 of the Title page, References Cited, Column 1, Line 39:

delete "at" and insert --et--.

On page 2 of the Title page, References Cited, Column 1, Line 40:

delete "Neuraminiclase" and insert --Neuraminidase--.

On page 2 of the Title page, References Cited, Column 1, Line 44:

delete "at" and insert --et--.

On page 2 of the Title page, References Cited, Column 2, Line 56:

delete "Fct" and insert --PCT--.